US011416991B2

(12) United States Patent
Tao et al.

(10) Patent No.: US 11,416,991 B2
(45) Date of Patent: Aug. 16, 2022

(54) FAST BACTERIA DETECTION AND ANTIBIOTIC SUSCEPTIBILITY TEST BY PRECISION TRACKING OF BACTERIAL CELLS

(71) Applicant: Arizona Board of Regents on behalf of Arizona State University, Scottsdale, AZ (US)

(72) Inventors: Nongjian Tao, Fountain Hills, AZ (US); Yunze Yang, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 351 days.

(21) Appl. No.: 16/644,453

(22) PCT Filed: Sep. 4, 2018

(86) PCT No.: PCT/US2018/049369
§ 371 (c)(1),
(2) Date: Mar. 4, 2020

(87) PCT Pub. No.: WO2019/050847
PCT Pub. Date: Mar. 14, 2019

(65) Prior Publication Data
US 2021/0065368 A1   Mar. 4, 2021

Related U.S. Application Data

(60) Provisional application No. 62/554,461, filed on Sep. 5, 2017.

(51) Int. Cl.
*G06T 7/00* (2017.01)
*C12Q 1/18* (2006.01)
(Continued)

(52) U.S. Cl.
CPC .............. *G06T 7/0014* (2013.01); *C12Q 1/18* (2013.01); *G06K 9/6201* (2013.01); *G06T 7/246* (2017.01);
(Continued)

(58) Field of Classification Search
None
See application file for complete search history.

(56) References Cited

U.S. PATENT DOCUMENTS

2009/0325210 A1*  12/2009  Weichselbaum ......... C12Q 1/04
                                                                                              435/29
2017/0045514 A1     2/2017  Tao et al.
(Continued)

FOREIGN PATENT DOCUMENTS

WO        2006066216 A2     6/2006

OTHER PUBLICATIONS

Aghayee et al. "Combination of fluorescence microscopy and nanomotion detection to characterize bacteria" Molecular Recognition, vol. 26, No. 11, 2013, pp. 590-595.
(Continued)

*Primary Examiner* — Matthew C Bella
*Assistant Examiner* — Brian D Shin
(74) *Attorney, Agent, or Firm* — Withrow & Terranova, P.L.L.C; Vincent K. Gustafson

(57) ABSTRACT

A system for identification of bacterial cells in free solution in a sample. A sample handler is adapted to position the sample. A light source illuminates a large volume of the sample. An imager is located to receive light scattered from the sample. A computer it is coupled to receive data transmitted from the imager. A controller is coupled to send control signals to the sample handler and the computer. The imager processes the scattered light to form images of the bacteria and transmits bacteria image information to the
(Continued)

computer, wherein the bacteria image information includes intensity values and position data for the bacteria images from which the computer determines the presence of bacteria.

21 Claims, 25 Drawing Sheets

(51) Int. Cl.
G06K 9/00 (2022.01)
H04N 5/00 (2011.01)
G06T 7/246 (2017.01)
G06T 7/73 (2017.01)
G06K 9/62 (2022.01)
H04N 5/225 (2006.01)
H04N 5/247 (2006.01)
G06V 10/60 (2022.01)
G06V 10/145 (2022.01)

(52) U.S. Cl.
CPC .............. G06T 7/73 (2017.01); G06V 10/145 (2022.01); G06V 10/60 (2022.01); H04N 5/2256 (2013.01); H04N 5/247 (2013.01); G06T 2207/30024 (2013.01)

(56) References Cited

U.S. PATENT DOCUMENTS

2017/0219999 A1    8/2017 Serabyn et al.
2018/0339293 A1*  11/2018 Miedl ..................... B01L 3/545

OTHER PUBLICATIONS

Baltekin et al. "Antibiotic susceptibility testing in less than 30 min using direct single-cell imaging" PNAS, vol. 114, No. 34, 2017, pp. 9170-9175.
Bauer et al. "Review of Rapid Diagnostic Tests Used by Antimicrobial Stewardship Programs" Clinical Infectious Diseases, vol. 59, Issue Supplement No. 3, 2014, pp. S134-S145.
Bergeron et al. "Preventing Antibiotic Resistance through Rapid Genotypic Identification of Bacteria and of Their Antibiotic Resistance Genes in the Clinical Microbiology Laboratory" Journal of Clinical Microbiology, vol. 36, No. 8, 1998, pp. 2169-2172.
Besant et al. "Rapid electrochemical phenotypic profiling of antibiotic-resistant bacteria" Lab Chip, vol. 15, No. 13, 2015, pp. 2799-2807.
Chantell, Christina "Multiplexed Automated Digital Microscopy for Rapid Identification and Antimicrobial Susceptibility Testing of Bacteria and Yeast Directly from Clinical Samples" Clinical Microbiology, vol. 37, No. 20, 2015, pp. 161-167.
Chen et al. "Rapid Antimicrobial Susceptibility Testing Using High Surface-to-Volume Ratio Microchannels" Analytical Chemistry, vol. 82, No. 3, 2010, pp. 1012-1019.
Choi et al. "A rapid antimicrobial susceptibility test based on single-cell morphological analysis" Science Translational Medicine, vol. 6, No. 267, 2014, 13 pages.
Choi et al. "Rapid antibiotic susceptibility testing by tracking single cell growth in a microfluidic agarose channel system" Lab on a Chip, vol. 13, No. 2, 2012, 8 pages.
Chotinantakul et al. "Advanced Amperometric Respiration Assay for Antimicrobial Susceptibility Testing" Analytical Chemistry, vol. 86, No. 20, 2014, pp. 10315-10322.
Davenport et al. "New and developing diagnostic technologies for urinary tract infections" Nature Reviews: Urology, vol. 14, No. 5, 2017, pp. 296-310.
Douglas et al. "Rapid Automated Microscopy for Microbiological Surveillance of Ventilator-associated Pneumonia" American Journal of Respiratory and Critical Care Medicine, vol. 191, No. 5, 2015, pp. 566-573.
Ertl et al. "Rapid Antibiotic Susceptibility Testing via Electrochemical Measurement of Ferricyanide Reduction by *Escherichia coli* and Clostridium sporogenes" Analytical Chemistry, vol. 72, No. 20, 2000, pp. 4957-4964.
Kinnunen et al. "Monitoring the growth and drug susceptibility of individual bacteria using asynchronous magnetic bead rotation sensors" Biosensors and Bioelectronics, vol. 26, No. 5, 2011, pp. 2751-2755.
Lissandrello et al. "Nanomechanical motion of *Escherichia coli* adhered to a surface" Applied Physics Letters, vol. 105, No. 11, 2014, pp. 113701.
Longo et al. "Rapid detection of bacterial resistance to antibiotics using AFM cantilevers as nanomechanical sensors" Nature: Nanotechnology, vol. 8, No. 7, 2013, pp. 522-526.
Lu et al. "Single Cell Antimicrobial Susceptibility Testing by Confined Microchannels and Electrokinetic Loading" Analytical Chemistry, vol. 85, No. 8, 2013, pp. 3971-3976.
Palmer et al. "Understanding, predicting and manipulating the genotypic evolution of antibiotic resistance" Nature Reviews: Genetics, vol. 14, Apr. 2013, pp. 243-248.
Reller et al. "Antimicrobial Susceptibility Testing: A Review of General Principles and Contemporary Practices" Clinical Infectious Diseases, vol. 49, Issue No. 11, Dec. 2009, pp. 1749-1755.
Schoepp et al. "Rapid pathogen-specific phenotypic antibiotic susceptibility testing using digital LAMP quantification in clinical samples" Science Translational Medicine, vol. 9, No. 410, 2017, 13 pages.
Sinn et al. "Asynchronous Magnetic Bead Rotation Microviscometer for Rapid, Sensitive, and Label-Free Studies of Bacterial Growth and Drug Sensitivity" Analytical Chemistry, vol. 84, No. 12, 2012, pp. 5250-5256.
Syal et al. "Antimicrobial Susceptibility Test with Plasmonic Imaging and Tracking of Single Bacterial Motions on Nanometer Scale" ACS Nano, vol. 10, Issue No. 1, 2016, pp. 845-852.
Syal et al. "Rapid antibiotic susceptibility testing of uropathogenic *E. coli* by tracking sub-micron scale motion of single bacterial cells" ACS Sensors, vol. 2, No. 8, 2017, pp. 1231-1239.
Yu et al. "Phenotypic antimicrobial susceptibility testing with deep learning video microscopy" Analytical Chemistry, vol. 90, No. 10, 2018, pp. 6314-6322.
International Search Report and Written Opinion for International Patent Application No. PCT/US2018/049369, dated Jan. 17, 2019, 15 pages.
International Preliminary Report on Patentability for International Patent Application No. PCT/US2018/049369, dated Mar. 10, 2020, 12 pages.

* cited by examiner

- DIFFERENTIATE BACTERIAL CELLS FROM OTHER MICRO-SCALE SUBSTANCES AND COMPARING TO PREDETERMINED VALUE FOR A BACTERIAL CELL 1410

- DETERMINING THE INTENSITY VARIATION PATTERN OVER TIME, AND COMPARING WITH REFERENCE PATTERNS FOR DEAD BACTERIAL CELLS 1412

- ANALYZING THE MOTION OF THE BRIGHT SPOT, AND COMPARE IT TO BROWNIAN MOTION 1414

- DETECTING SPLITTING OF A BRIGHT SPOT INTO TWO OR MORE SPOTS 1416

- DETERMINING THE TOTAL NUMBER OF BRIGHT SPOTS AND TRACK THEM OVER TIME 1418

- COMBINING FEATURES COMPARING THEM WITH THOSE FOR DEAD BACTERIAL CELLS AND OTHER MICRO-SCALE SUBSTANCES 1420

FAST BACTERIA DETECTION AND ANTIBIOTIC SUSCEPTIBILITY TEST BY PRECISION TRACKING OF BACTERIAL CELLS

TECHNICAL FIELD

The present invention relates to fast bacteria detection, identification (ID) and antibiotic susceptibility testing (AST), and, more particularly, to a method and apparatus for fast detection of bacterial cells in free solution using precision tracking of phenotypic features of bacterial cells.

BACKGROUND

Timely diagnosis of bacterial infection, and determination of appropriate antibiotic drugs save lives and reduce pain. Currently, healthcare providers often use a dipstick method to identify bacterial infection. The dipstick method is simple and relatively low cost, but it is inaccurate. Optical microscopy obtains a high-resolution image of the patient sample, which is used to identify bacterial cells, and possibly perform antibiotic susceptibility test. However, optical microscopes are bulky, expensive and difficult to use. More importantly, traditional optical microscopy obtains high spatial resolution images of the patient's sample at the expense of providing only a small field of view. This limits one to examine only a small sample volume at a time, which makes it difficult to find bacterial cells in a low concentration sample. For example, for a clinically relevant urine sample with bacterial infection, the concentration of bacteria is ~$10^5$ CFU/mL. For a typical high-resolution microscope, the view volume is less than $10^{-7}$ mL, so the average number of bacterial cells is less than 1. To image bacterial cells in the patient sample, sample enrichment is required, which adds additional difficulty and burden to use the technology. In addition, traditional optical imaging method requires immobilizing bacterial cells on a surface or in a gel matrix to obtain clear images, which adds extra steps in the sample preparation, and even worse, affects phenotypic features, such as growth and motion, of the bacterial cells. Furthermore, the traditional optical microscopy method relies on static images of the bacterial cells, which miss the motions of bacteria. For these reasons, optical microscopy technology is rarely used by the healthcare provider at the point of care. Typically, the healthcare provider must send the patient sample to a clinical lab for analysis.

State-of-the-art for ID/AST

ID/AST (Identification/ antibiotic susceptibility testing) methods fall into two categories: genotypic- and phenotypic-based methods[1-3], with the former detecting antibiotic resistance genes or genetic mutations conferring resistance[4,5]. While these genotypic approaches are useful, they require a prior knowledge of resistance genes or specific genetic mutations, and are not applicable to phenotypic antibiotic resistance evolved from multiple mechanisms.

For these reasons, AST technologies based on tracking phenotypic features have been pursued. Recent examples include magnetic detection[6,7], optical imaging of bacterial growth[8-13], and electrochemical detection of metabolic activity-related biochemical signatures[14-16]. Another phenotypic method is to track the metabolic-driven motion and growth using atomic force microscope (AFM)[17-19], plasmonic microscopy[20], optical microscopy[21,22], or detect the growth with microfluidics[23] or using biochemical amplification[24]. These techniques typically require immobilization of bacteria on a surface[25], in a gel, or in microfluidic channels for imaging or detection, which raises practical difficulties in testing clinical samples, and affects the growth of the bacterial cells, and thus extraction of growth- and motion-related phenotypical features. In addition, most of these methods do not work on clinically-relevant concentrations, procedures such as culturing and enriching of the clinical samples, followed by bacterial isolation and purification are still required.

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

A system for identification of bacterial cells in free solution in a sample is disclosed. A sample handler is adapted to position the sample. A light source illuminates a substantially large volume of the sample. An imager is located to receive light scattered from the bacterial cells or other particles suspended in the illuminated volume of the sample. A computer is coupled to receive data transmitted from the imager. A controller is coupled to send control signals to the sample handler and the computer. The imager processes the scattered light to form images of the bacteria and transmits bacteria image information to the computer, wherein the bacteria image information includes intensity values and position data for the bacteria images from which the computer determines the presence of bacteria.

In one aspect, the present disclosure describes apparatus and algorithms to overcome the limitations of the traditional microscopy related to fast bacteria detection with minimal sample preparation and yet maximal phenotypic feature extraction. By precision tracking of phenotypic features of bacterial cells, the presence or absence of bacterial cells in the patient sample (e.g., urine, blood and sputum), and identity of the bacterial infection are determined. The methods and systems disclosed also provide tests for antibiotic susceptibility by analyzing if an antibiotic inhibits the bacterial cells. The first capability allows the healthcare provider to determine if bacteria infect the patient and the type of bacteria. The second capability further allows the healthcare provider to determine which antibiotic works the best for the particular infection. In addition to medical applications, the technology disclosed here can also detect bacteria in drinking water, beverage and food or air (airborne bacteria).

BRIEF DESCRIPTION OF THE DRAWINGS

While the novel features of certain embodiments of the invention are set forth with particularity in the appended claims, the invention, both as to organization and content, will be better understood and appreciated, along with other objects and features thereof, from the following detailed description taken in conjunction with the drawings, in which:

FIG. 12-FIG. 14 show examples of sub-algorithms implemented in the computer or by using electronic circuitry.

Figures 1A, 1B:
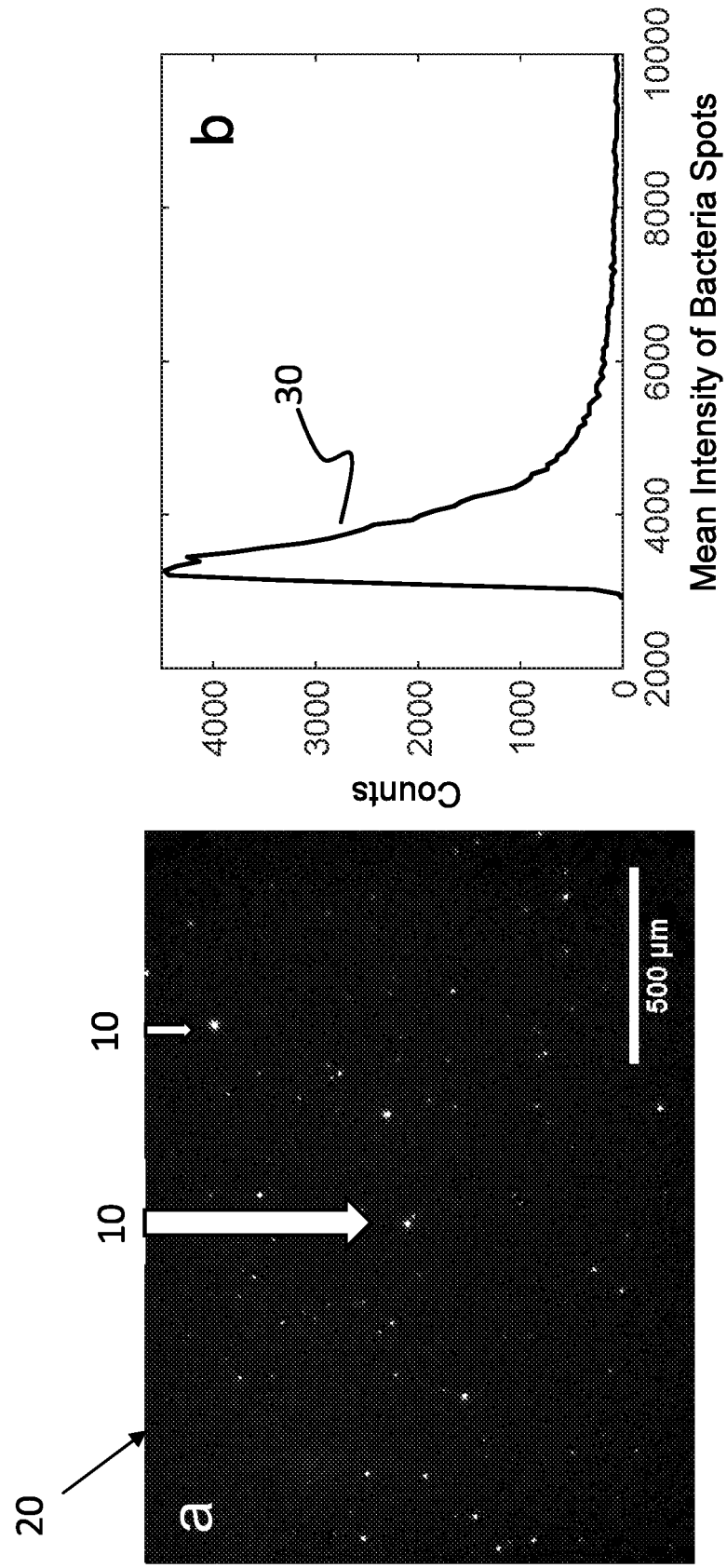
FIG. 1A shows an example of bacteria imaging using light-sheet scattering microscopy.
FIG. 1B shows an example of intensity distribution of bright areas corresponding to the image in FIG. 1A.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

The following disclosure describes a system and method for fast detection of bacteria using precision tracking of phenotypic features of bacterial cells. Several features of methods and systems in accordance with example embodiments are set forth and described in the figures. It will be appreciated that methods and systems in accordance with other example embodiments can include additional procedures or features different than those shown in the figures. Example embodiments are described herein with respect to systems and methods for determining the presence of bacteria, for bacteria ID (identification) and for AST (antibiotic susceptibility testing). However, it will be understood that these examples are for the purpose of illustrating the principles, and that the invention is not so limited.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Innovations of the Present Disclosure

1. Free Solution

The present disclosure directly works on solution-phase clinical samples for real-time culture-free imaging and detection. In other words, the bacterial cells are not attached to a surface, a medium or any substance such that they can grow, divide and move freely without restrictions. The benefits of the examples presented herein include: 1) minimum sample preparation is involved in the test, no culturing-based enrichment is needed; 2) the test presented works directly on original patient samples, no pathogen isolation is required; 3) the test works in free solution, which allows a normal growth and division of pathogens with minimum perturbation to the cells for identification and antimicrobial susceptibility testing; 4) free solution detection also allows extraction of multiple phenotypic features of individual single cell, including cell size, morphology, motion, rotation and division. 5) real-time imaging and analysis provide the utmost rapid results for both pathogen identification and rapid antimicrobial susceptibility test.

2. Large Imaging Volume

The present disclosure provides a large-volume imaging capability to measure raw urine samples to cover the clinically relevant range. Traditionally, the increase of the field of view or imaging volume results in a decrease of imaging resolution, which makes the optical system insensitive to small objects such as bacteria. Features such as the cell morphology, the translational and rotational motion are unraveled in the image and difficult to extract. In this present disclosure, we use the disclosed algorithm to extract these features from the intensity profiles of each bacterium/particle without resolving it from the image. We also use video microscopy to track the changes of these features over time for single bacterium/particle for further identification and antimicrobial susceptibility testing. The inventors have carried out comprehensive experiments and concluded that the optimal volume range is between $10^{-5}$ mL and $10^{-2}$ mL. Smaller volumes than $10^{-5}$ mL as used in some of the prior arts[25] make it hard to find a bacterial cell in the sample containing bacterial cells within clinically relevant concentrations. For example, an imaging volume of $10^{-5}$ mL for a patient sample with a clinically relevant concentration of $\sim 10^5$ cells per mL contains only one bacterial cells, which is inadequate for ID nor AST. On the other hand, volumes higher than $10^{-2}$ mL make it difficult to capture sufficient light from each bacterial cells and image optically with state of the art optical imaging techniques. A high intensity light source could be used to increase the light level, but, this may perturb the natural physiological status of the bacterial cells, and also heating of the sample, leading to thermal drift and other issues for forming clear optical images of the cells. The limited light intensity resulted from large imaging volumes also require longer exposure time, which makes it hard to track rapid motion of the bacterial cells in free solution.

3. Video-Microscopy-Based Single Bacterium/Particle Tracking Over Time in Free Solution The single bacterium/particle tracking and analysis capability are unique and critical for this disclosure. It is different from the traditional approach that measuring the average intensity from many cells as in the light scattering-related technologies. It is also different from static image analysis or the time-lapse measurement that only intermittently access to the sample over a long period of time. We record the sample using video microscopy for tracking bacterium/particle traces over time and do analysis on individual bacteria cells. First, it allows us to track individual bacterium/particle over time, from which, we extract intrinsic features such as the cell size, morphology, motion, rotation, cell number and cell division events. Many of these features are unobtainable in static image analysis, light-scattering analysis or time-lapse imaging. Second, single cell detection capability enables the identification at single particle level, which is more accurate and particle-specific. This identification at single cell level also provides a single-cell feature-based digital filter for anticipated pathogens, which is of vital importance in mixed samples, and extremely crucial in applications such as antimicrobial susceptibility testing in real patient samples. Third, single particle tracking provides statistical power for feature analysis, which is necessary to achieve the utmost rapid determination of pathogens and in antimicrobial susceptibility testing. Fourth, single particle imaging provides both cell numbers and feature changes in morphology and mass for each individual cell, instead of the total biomass of many bacteria that counted in light scattering cases. This is important in cases such as in testing drugs that only affect the cell splitting, but not cell growth. Finally, this single particle approach is insensitive to common noises in the system, which is much more robust and accurate.

Challenges Solved by this Disclosure

1) Bacteria grows much faster in free solution than in solid phase such as a surface, a gel, or a confined microfluidic channel. Patient samples are also typically in solution phase. Thus, detection pathogens in free solution phase is of critical importance to the success of the present invention. However, measuring single bacterial cells in free solution is difficult, because bacterial cells move both actively due to their intrinsic metabolism and passively under the influence of thermal motion (Brownian motion) and mechanical drift arising from non-uniform temperature or other mechanical perturbations in a 3-dimensional environment. Both hardware (such as illumination criteria, optical configuration) and software (such as tracking and feature extraction) innovations are needed to visualize single bacterial cells for reliable analysis. 2) Bacterial cells are typically small (a few micrometers). To examine single bacterial cells, the common practice is to attach them on a fixed surface to prevent their motions and then image them with a high resolution optical microscope, as disclosed in the prior arts. High-resolution optical microscopy results in a limited viewing area or imaging volume, which is insensitive to samples with low yet clinically relevant concentrations of bacterial cells in a patient sample. If a low-zoom or low resolution optical imaging setting is used to increase the imaging volume, then the morphology of each bacterial cell cannot be resolved and image contrast is poor due to limited light intensity that each bacterial cell receives and limited number of today's CCD or CMOS imagers.

To overcome these challenges, we developed large volume imaging setup and imaging algorithm. The optical setup includes configurations that reduce background noise that help maximize the image contrast of bacterial cells. The imaging algorithm allows us to extract features of single bacterial cells, such as size, morphology, motion, rotation, division etc. in the low-resolution (but high contrast) optical setup without having to resolve each of them. 3) To achieve utmost rapid determination of the identification of the pathogen and the antimicrobial susceptibility testing, we track the individual bacterial cells over time and from which we monitor multiple features and their changes over time. We combine all these features for the fastest ID and AST.

The present disclosure overcomes these challenges with several innovations.
1) Bacterial cells are imaged in free solution (urine or blood) without immobilizing or attaching the cells on a surface or gel matrices. This simplifies sample preparation and also provides the cells an environment to grow, divide and move (rotate or migrate from one location to another). The latter is important because phenotypic AST relies on detecting a phenotypic feature, such as growth or motion.
2) A large imaging volume technology is used to increase the likelihood of capture sparse bacterial cells in a patient urine or blood sample.

Implementing this free-solution and large imaging volume apparatus and method is non-trivial because of various difficulties and we have carried out many experiments and developed unique solutions to overcome them.
1) In free solution, bacterial cells move rapidly due to their motility, thermal motion and mechanical drift. We developed accurate tracking algorithms to follow each bright spot (bacterial cells or other substances in the sample) in the image over time, and determine the number, imaging intensity and position at each moment.
2) The use of large imaging volume makes it difficult to resolve the morphology of each bacterial cell in the free solution. We overcome this difficulty by focusing on tracking the total intensity of each bacterial cell over time and obtain morphology information from the total intensity and intensity variation over time. Additionally, we track the position of each cell over time with a precision algorithm that allows tracking of the thermal motion (Brownian motion) and motility of the cell, which provides additional information on the size and activity of the cell.

Definitions

Generally, as used herein, the following terms have the following meanings when used within the context of microarray technology:

The articles "a" or "an" and the phrase "at least one" as used herein refers to one or more.

As used herein, "AST" means antibiotic susceptibility testing of cells. Antibiotic susceptibility testing (AST) is used to identify antibiotic resistant bacterial strains and to enable treatment with appropriate antibiotics.

As used herein, "plurality" is understood to mean more than one. For example, a plurality refers to at least two, three, four, five, ten, 25, 50, 75, 100, 1,000, 10,000 or more.

As used in this specification, the terms "computer", "processor" and "computer processor" encompass a personal computer, a tablet computer, a smart phone, a microcontroller, a microprocessor, a field programmable object array (FPOA), a digital signal processor (DSP), an application-specific integrated circuit (ASIC), a field programmable gate array (FPGA), a programmable logic array (PLA), or any other digital processing engine, device or equivalent capable of executing software code including related memory devices, transmission devices, pointing devices, input/output devices, displays and equivalents.

"Obtaining" is understood herein as manufacturing, purchasing, or otherwise coming into possession of.

"Free solution" herein means that bacterial cells can grow, divide or move freely, such that the growth, motion, metabolism of the cells are not restricted or affected by the means associated with immobilization, such as surface, gel or matrix.

"ID" refers to identification of bacteria.

Example Embodiments

The system disclosed herein overcomes the drawbacks of the traditional optical microscopy technology with a low spatial resolution imaging system. The imaging system features a large field of view so that it can image a large sample volume and determine the presence and absence of bacterial cells in the patient sample without sample enrichment. For an image volume of 1 µL, the number of bacterial cells is ~100 for a concentration of ~$10^5$ CFU/mL. The increased imaging volume lowers the spatial resolution of the imaging technology, making it hard to differentiate bacterial cells from other substances in the sample using the traditional imaging analysis algorithm. The present invention describes an apparatus for large sample volume imaging and further discloses algorithms to extract key phenotypic features of bacteria for identification and antibiotic susceptibility test.

The phenotypic features include: 1) image intensity of each bacterial cell, 2) position of the cell, and 3) changes of the intensity and position over time, and before and after antibiotic treatment. A typical patient sample contains various substances that will also scatter light. For example, in urine samples, there are micro-scale crystals, and white blood cells and other micron-scale substances. However, the phenotypic features are unique for bacteria, and distinctly different from other substances in the patient sample. This is because of the following reasons:
1) Light scattering intensity is sensitive to the size, shape and refractive index of the object, and substances that are larger or smaller than bacterial cells, or different in terms of shapes and optical refractive indices, scatter light with intensities substantially different from those from the bacteria.
2) Bacterial cells move in solution due to swimming, swamping or other metabolic activities. These motions lead to distinct changes in the scattered intensity. For example, flagella motions in motile bacteria cause large fluctuations in the scattered light, which is different from other substances. Bacterial cells may also rotate, and also cause large intensity fluctuations.
3) Bacteria motions can be also tracked from the position of each bacteria cell. The low resolution imaging system disclosed here images each bacterial cell as a bright spot. By tracking the position of each bacterial cell, precise motions of the bacterial cell from one position to another can be determined and analyzed, as they are distinctly different from other substances in the patient sample.
4) A combination of the intensity, position, and changes in intensity and position, further improves the identification accuracy.

Algorithms used to track the intensity, position, and changes in intensity and position of a bacterial cell are described below.

In one example, tracking is based on procedures of subpixel spots localization and track linking. First, spots (bacterial cells or other micro-scale substances in the sample) in each video frame are recognized using Difference of Gaussian (DoG) algorithm and localized to pixel level by finding local maximum. Other algorithms with local maximum finding can also be applied in this step. The accurate subpixel position is recalculated by locally fitting with a quadratic function or Gaussian function. Intensities, x and y positions of each spots on each frame are extracted after subpixel localization. Detected spots can be filtered with different criteria, including intensity threshold, contrast, signal-to-noise level etc. The next step is to link spots in each frame as a track. Linear Assignment Problem (LAP) trackers are used to connect spots over time. A cost matrix form frame-to-frame linking is used and linking cost is calculated. The spots are linked in a way that minimize the cost function. Other track linking algorithm with cost function minimization can also be applied to the spots connection. After a track is generated, track parameters, including speed, and displacement of each track, are calculated.

Mean intensities of each spot are calculated after spots are recognized and localized with sub-pixel resolution. During spot recognition, a cut-off threshold is manually set to filter out low contrast spots, which have lower intensity level than bacteria value. High intensity spots can be further filtered out after recognition according to the intensity distribution of bacteria. Bacteria spots have predetermined intensity range from 1000~30000 for 16 bit images for illumination using laser of ~100 mW).

Bacteria Imaging Using a Low Amplification and Large View Volume Light Scattering Microscopy Referring now to FIG. 1A, an example of bacteria imaging using light-sheet scattering microscopy is shown. A light-sheet scattering microscope was used to image a sample of E. coli in water. A typical sample image 20 from a region of interest (ROI) in the sample was obtained using light-sheet scattering microscopy. Each bright area 10 in the sample image 20 is an image of a single bacteria.

Referring now to FIG. 1B, an example of intensity distribution of bright areas corresponding to the image in FIG. 1A is shown. Curve 30 is a plot of bacteria count on the Y axis versus the mean intensity of bacteria spots on the X axis.

Phenotypic Features from Motions (Positions and Position Changes)

Figure 2:
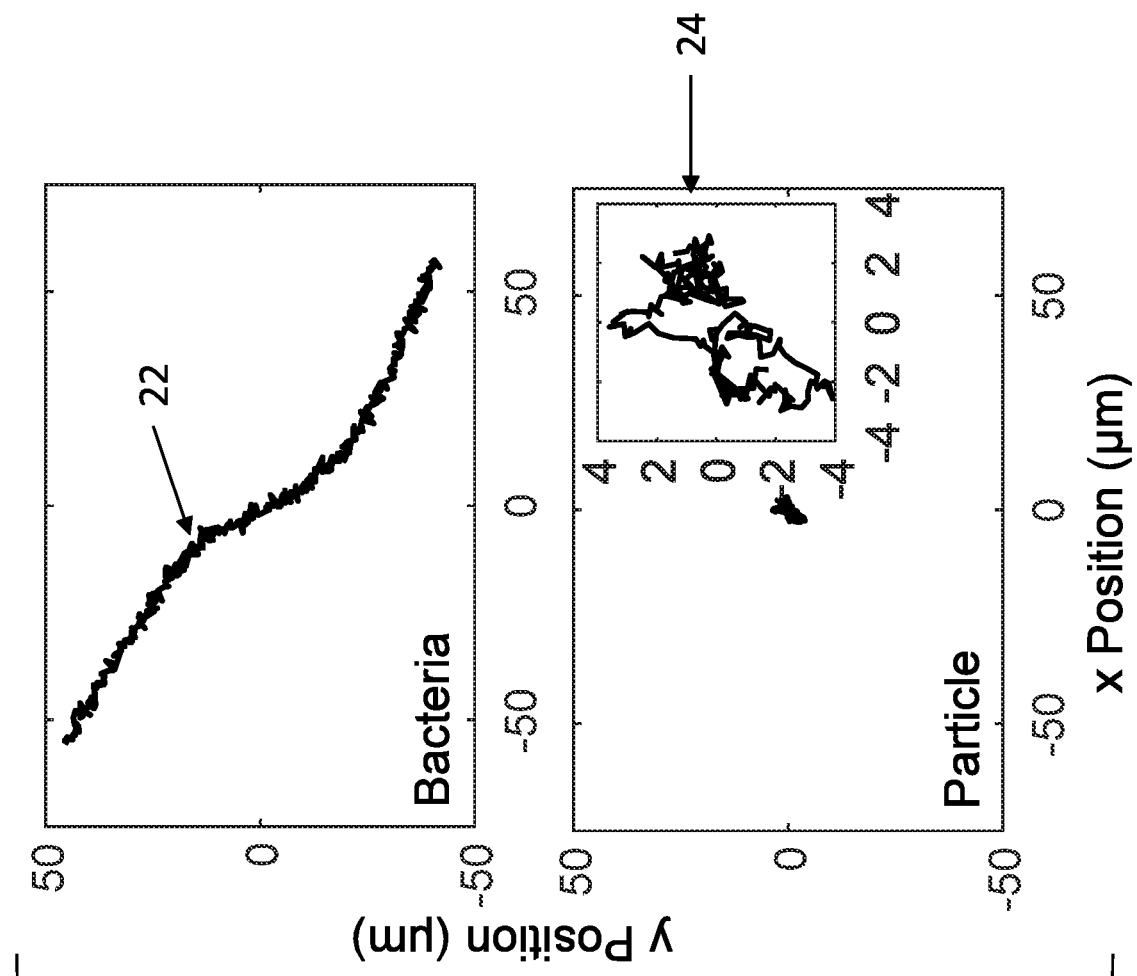
FIG. 2 shows an example comparing typical trajectory of bacteria (top panel) and 0.5 μm polystyrene particle (bottom panel).

Referring now to FIG. 2, an example of typical trajectory of bacteria (top panel) and 0.5 µm polystyrene particle (bottom panel) is shown. In one example, the directional motion of bacterial cells was compared to 0.5 µm polystyrene particles. Bacteria shows a directional motion as indicated by curve 22. A particle in solution is limited by Brownian motion of the particle as indicated by expanded view 24.

Figure 3:
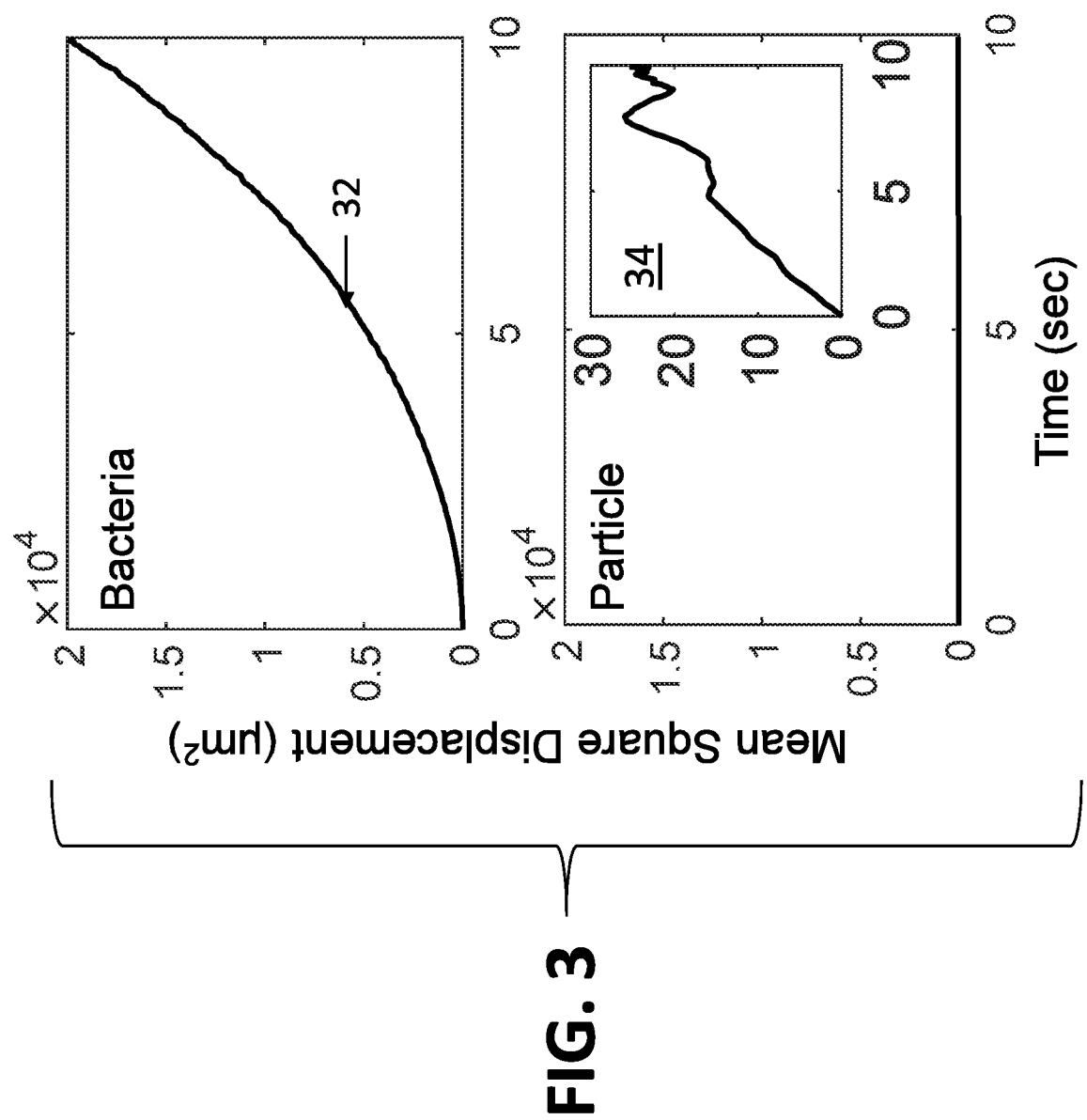
FIG. 3 shows an example comparing mean square displacement (MSD) of the trajectory of bacteria (top panel) and 0.5 μm polystyrene particle (bottom panel).

Referring now to FIG. 3, mean square displacement (MSD) of the trajectory of bacteria (top panel) and 0.5 µm polystyrene particle (bottom panel) is shown. Bacteria shows a faster increase of MSD over time while the MSD of the particle is linear as indicated by comparing curve 32 with the expanded view of the particle shown in plot 34.

Figure 4:
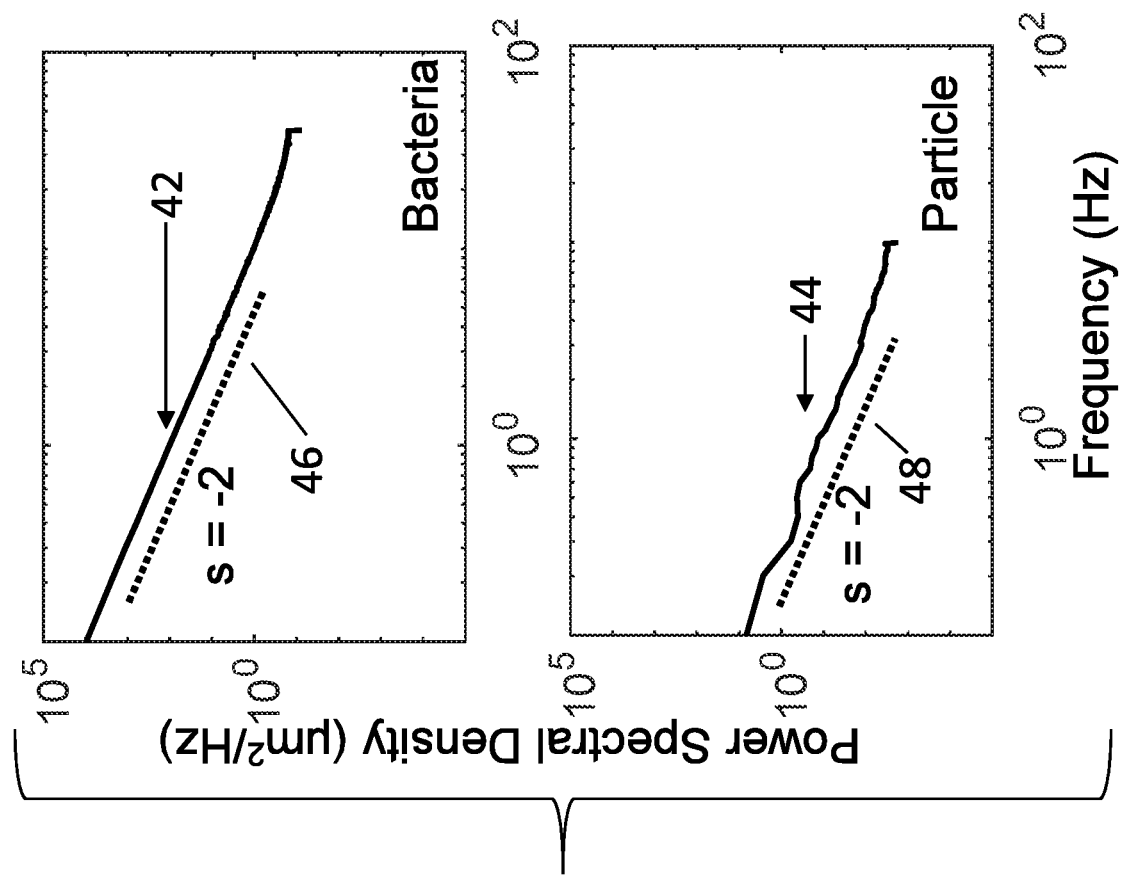
FIG. 4 shows an example comparing power spectral density (PSD) of displacement of bacteria (top panel) and particle (bottom panel).

Referring now to FIG. 4, an example of power spectral density (PSD) of displacement of bacteria (top panel) and particle (bottom panel) is shown. Curve 42 shows power spectral density of bacteria plotted against frequency in Hz. Curve 44 shows power spectral density of a particle plotted against frequency in Hz. The slope of both bacteria and particle are close to −2 (shown in dashed lines 46, 48 in both panels).

Phenotypic Features from Intensity Profiles

Figure 5A:
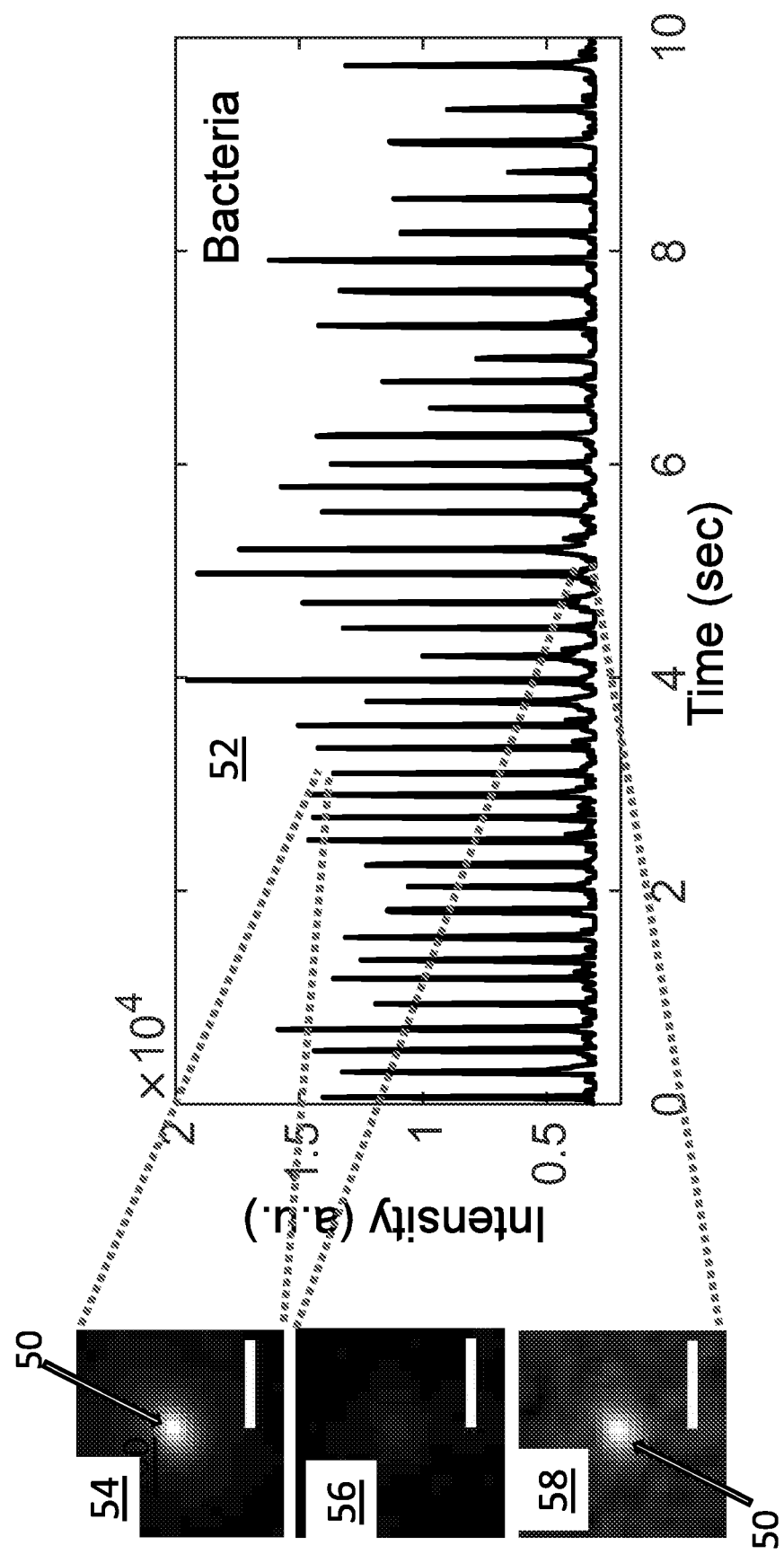
FIG. 5A shows an example of a plot of bacteria image intensity over time is shown with example images at specific time coordinates.

Referring now to FIG. 5A, an example of a plot of bacteria image intensity over time is shown with example images at specific time coordinates. Plot 52 is a plot of a typical bacteria image intensity profile for a sample that was imaged continuously over 10 seconds. Snapshot images 54, 56 and 58 of a bacterial cell 50 were acquired over time and correlate to specific times on the plot as indicated by the broken lines. Note that the image contrast in snapshot image 54 is enhanced for clarity in the panel 56.

Figures 5B, 5C:
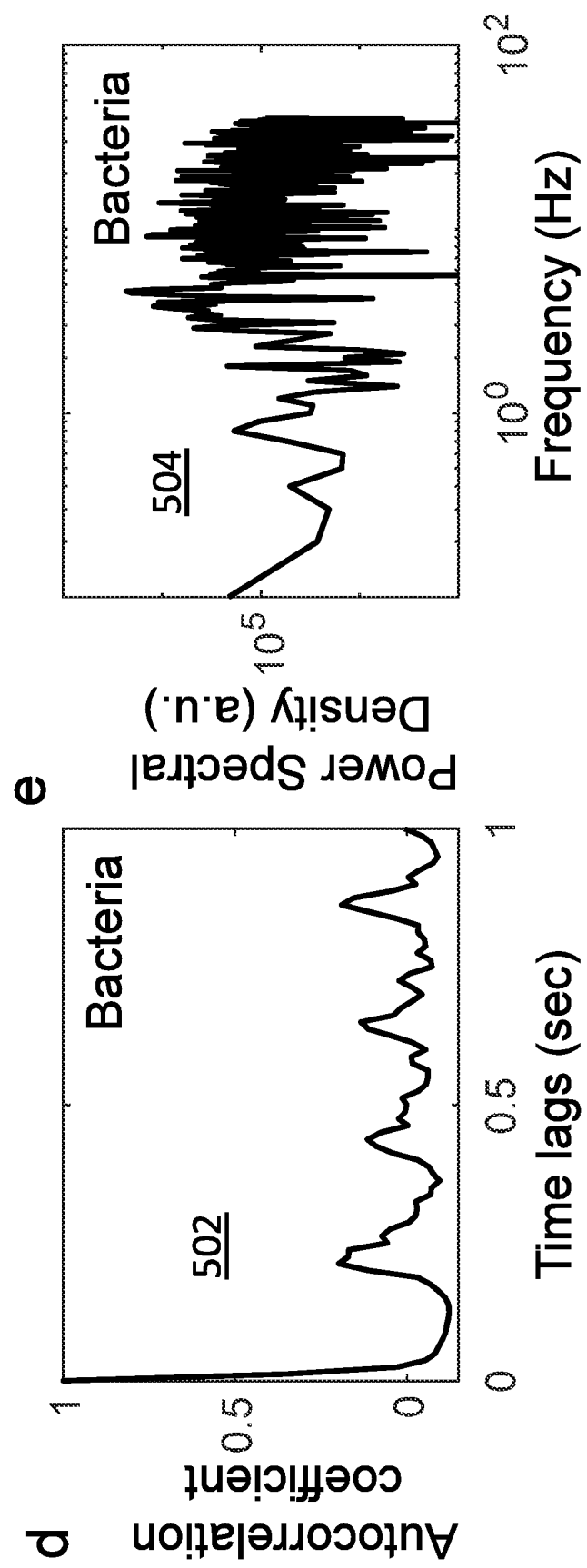
FIG. 5B shows a plot of an autocorrelation coefficient of the intensity profile of bacteria.
FIG. 5C shows an example of a plot of power spectral density of an intensity profile of bacteria.

Referring now to FIG. 5B, a plot of an autocorrelation coefficient of the intensity profile of bacteria is shown. Plot 502 represents the autocorrelation coefficient of the intensity profile of a bacterial cell as plotted against time lags in seconds.

Referring now to FIG. 5C, an example of a plot of power spectral density of an intensity profile of bacteria is shown. Plot 504 represents the power spectral density of intensity profile of a bacterial cell plotted against frequency in Hz.

Figure 5D:
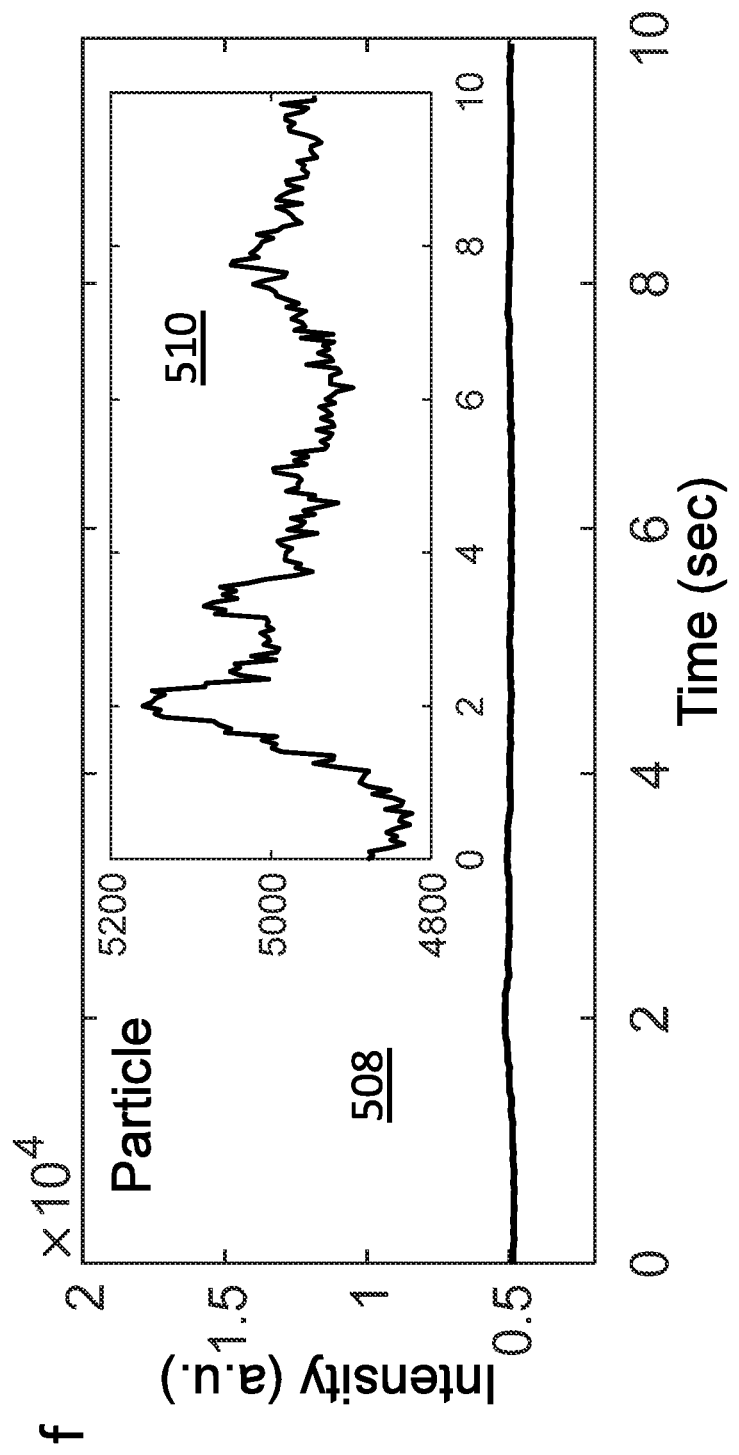
FIG. 5D shows a typical intensity profile of 0.5 micrometer polystyrene beads. Inset is the increased magnification profile of the particle.

Referring now to FIG. 5D, a typical intensity profile of 0.5 micrometer polystyrene beads is shown. Plot 508 represents intensity of the imaged particles versus time. Inset 510 shows the profile of the particle at an increased magnification.

Figures 5E, 5F:
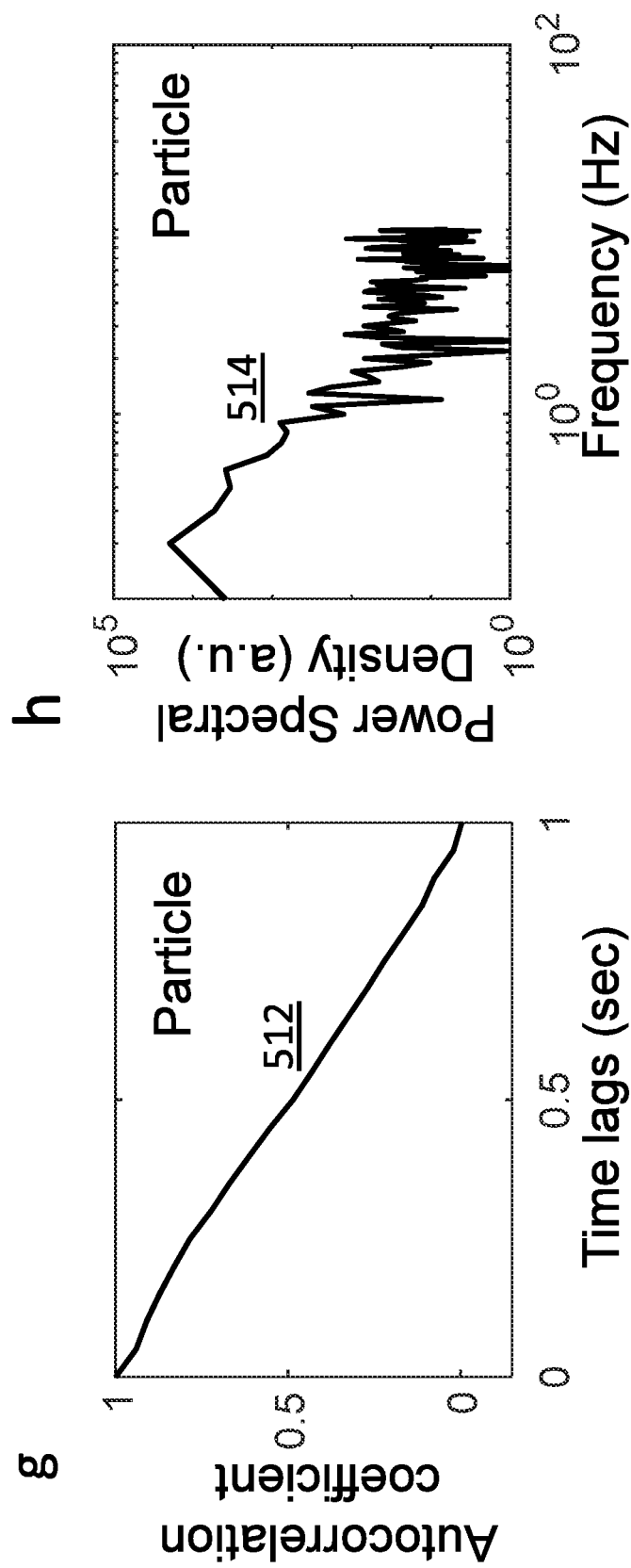
FIG. 5E is a plot of the autocorrelation coefficient of the intensity profile of the particle.
FIG. 5F is a plot of the spectral density of the intensity profile of the particle.

Referring now to FIG. 5E, a plot of the autocorrelation coefficient of the intensity profile of the particle is shown. Plot 512 represents the coefficient of the intensity profile of a polystyrene particle plotted against time lags in seconds.

Referring now to FIG. 5F, a plot of the spectral density of the intensity profile of the particle is shown. Plot 514 represents the power spectral density of intensity profile of the polystyrene particle plotted frequency in Hz.

3D Trajectory of Combined Position (Motion) and Intensity Features

Figure 6A:
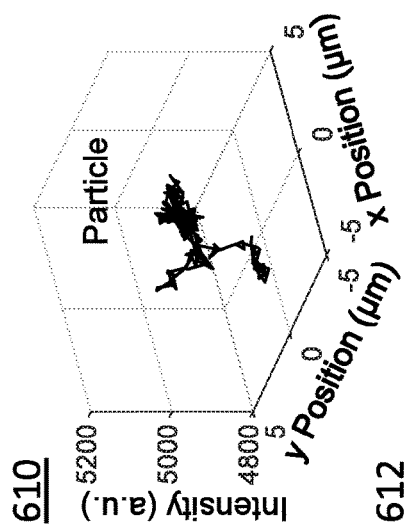
FIG. 6A shows a representative 3D trajectory of 0.5 μm polystyrene particles of combined position and intensity features.

Referring now to FIG. 6A, representative 3D trajectory of 0.5 µm polystyrene particles of combined position and intensity features is shown. Plot 610 is representative of the 3D trajectory of 0.5 µm polystyrene particles of combined position and intensity features.

Figure 6B:
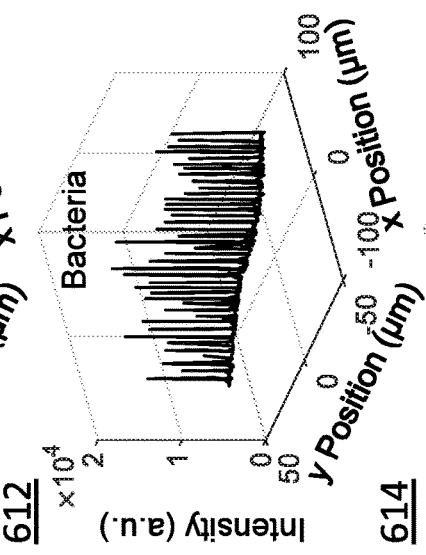
FIG. 6B shows an example of a plot of representative 3D trajectory of bacteria cells of combined position and intensity features.

Referring now to FIG. 6B, an example of a plot of a representative 3D trajectory of bacteria cells of combined position and intensity features is shown. Plot 612 is representative of the 3D trajectory of bacteria cells of combined position and intensity features.

Figure 6C:
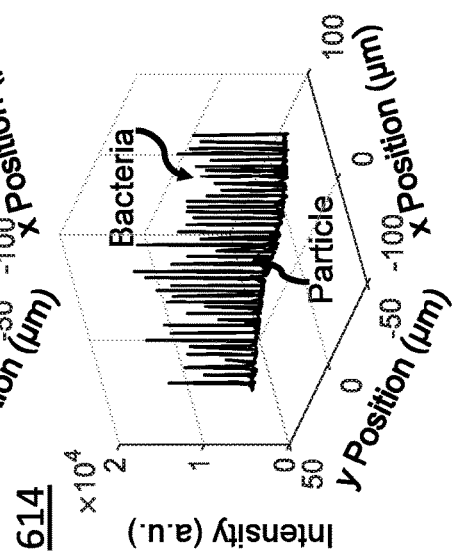
FIG. 6C shows a plot of 3D trajectory of 0.5 μm polystyrene particles and bacteria cells of combined position and intensity features at the same scale.

Referring now to FIG. 6C, a plot of a 3D trajectory of 0.5 µm polystyrene particles and bacteria cells of combined position and intensity features at the same scale is shown. Plot 614 is representative of the 3D trajectory of 0.5 µm polystyrene particles and bacteria cells of combined position and intensity features at the same scale.

Figures 6D, 6E, 6F:
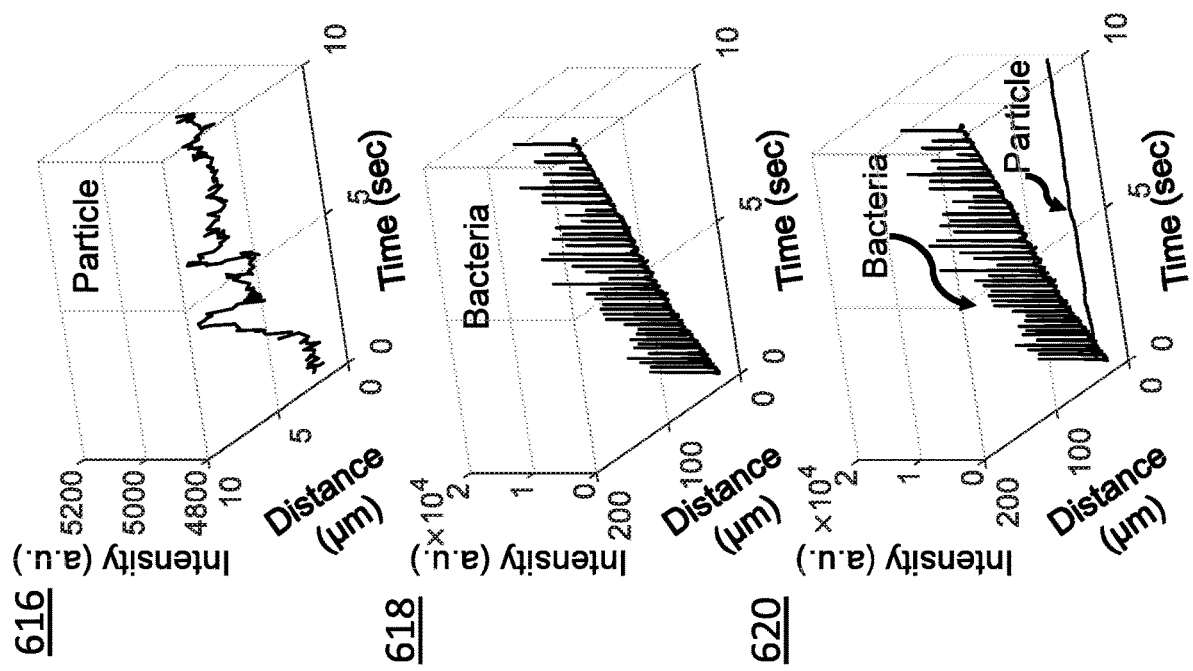
FIG. 6D shows a representative 3D trajectory of 0.5 μm polystyrene particles of combined displacement, time and intensity features.
FIG. 6E shows a representative 3D trajectory of bacteria cells of combined displacement, time and intensity features.
FIG. 6F shows a plot of 3D trajectory of 0.5 μm polystyrene particles and bacteria cells of combined displacement, time and intensity features at the same scale.

Referring now to FIG. 6D, a representative 3D trajectory of 0.5 µm polystyrene particles of combined displacement, time and intensity features is shown. Plot 616 is representative of the 3D trajectory of 0.5 µm polystyrene particles of combined displacement, time and intensity features.

Referring now to FIG. 6E, a representative 3D trajectory of bacteria cells of combined displacement, time and intensity features is shown. Plot 618 is representative of the 3D trajectory of bacteria cells of combined displacement, time and intensity features.

Referring now to FIG. 6F, a plot of 3D trajectory of 0.5 µm polystyrene particles and bacteria cells of combined displacement, time and intensity features at the same scale is shown. Plot 620 is representative of the 3D trajectory of 0.5 µm polystyrene particles and bacteria cells of combined displacement, time and intensity features at the same scale.

Differentiation of Bacterial Cells from Polystyrene Particles

Referring now to FIG. 7A-FIG. 7D, representative frames from videos of mixed bacteria and 0.5 µm polystyrene particles are shown. Bacteria cells 50 and particles 60 are shown in broken line circles. The scale bar in each frame is calibrated at 50 µm.

Figure 7A:
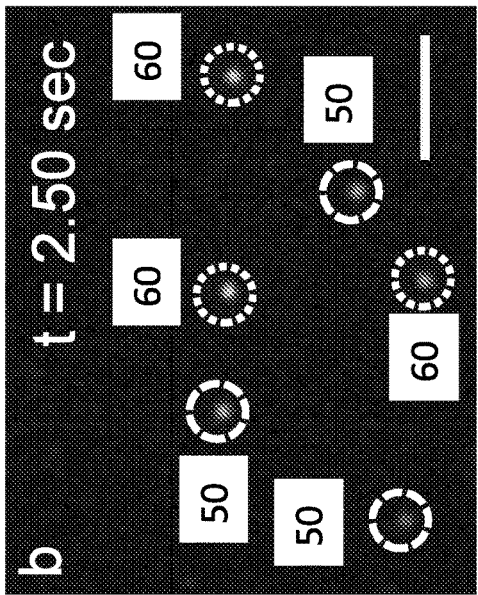
FIG. 7A-FIG. 7D show representative frames from videos of mixed bacteria and 0.5 μm polystyrene particles.
Figure 7B:
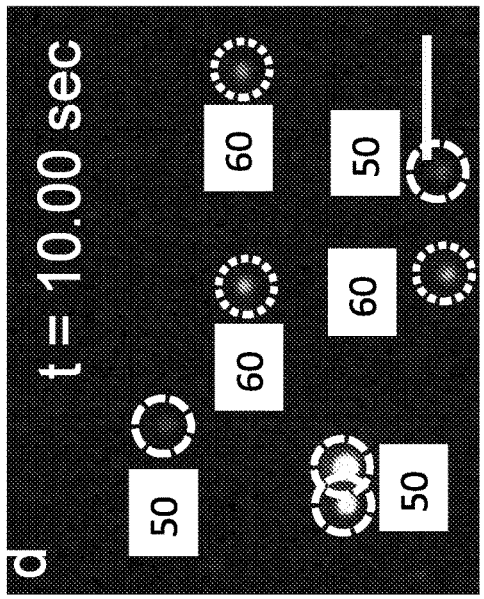
Figure 7C:
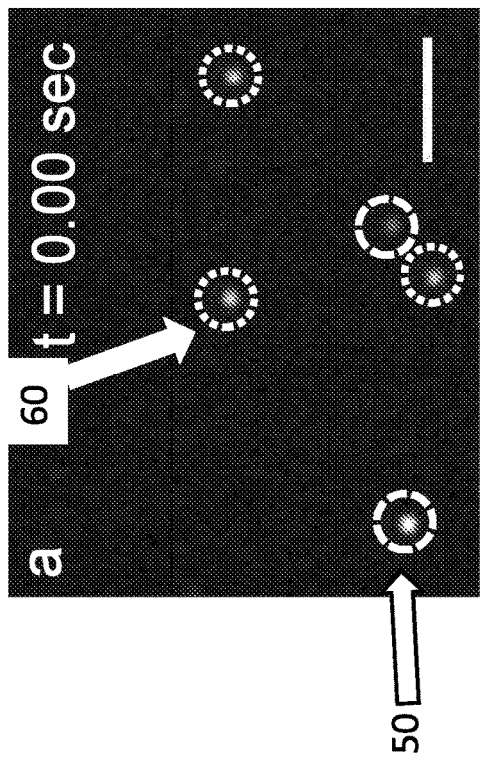
Figure 7D:
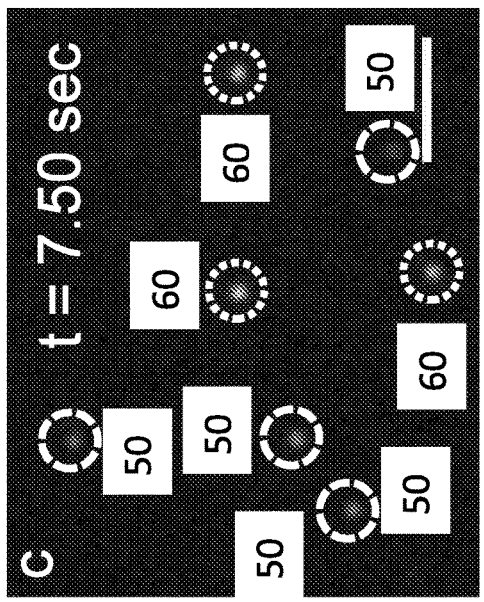
Figure 7E:
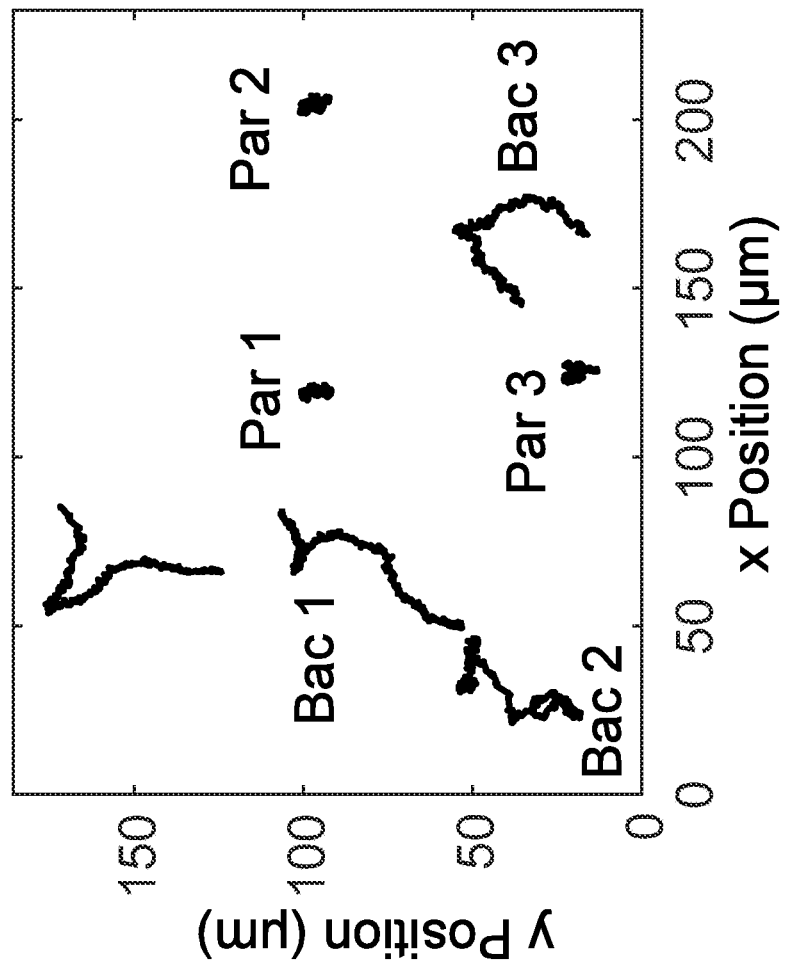
FIG. 7E shows some example trajectories of bacteria and particles in the video.

Referring now to FIG. 7E, an example of trajectories of bacteria and particles derived from a video tracking particles and bacteria over time is shown. Particles are labeled as Par 1-3. Bacteria are labeled as Bac 1-3.

Figure 7F:
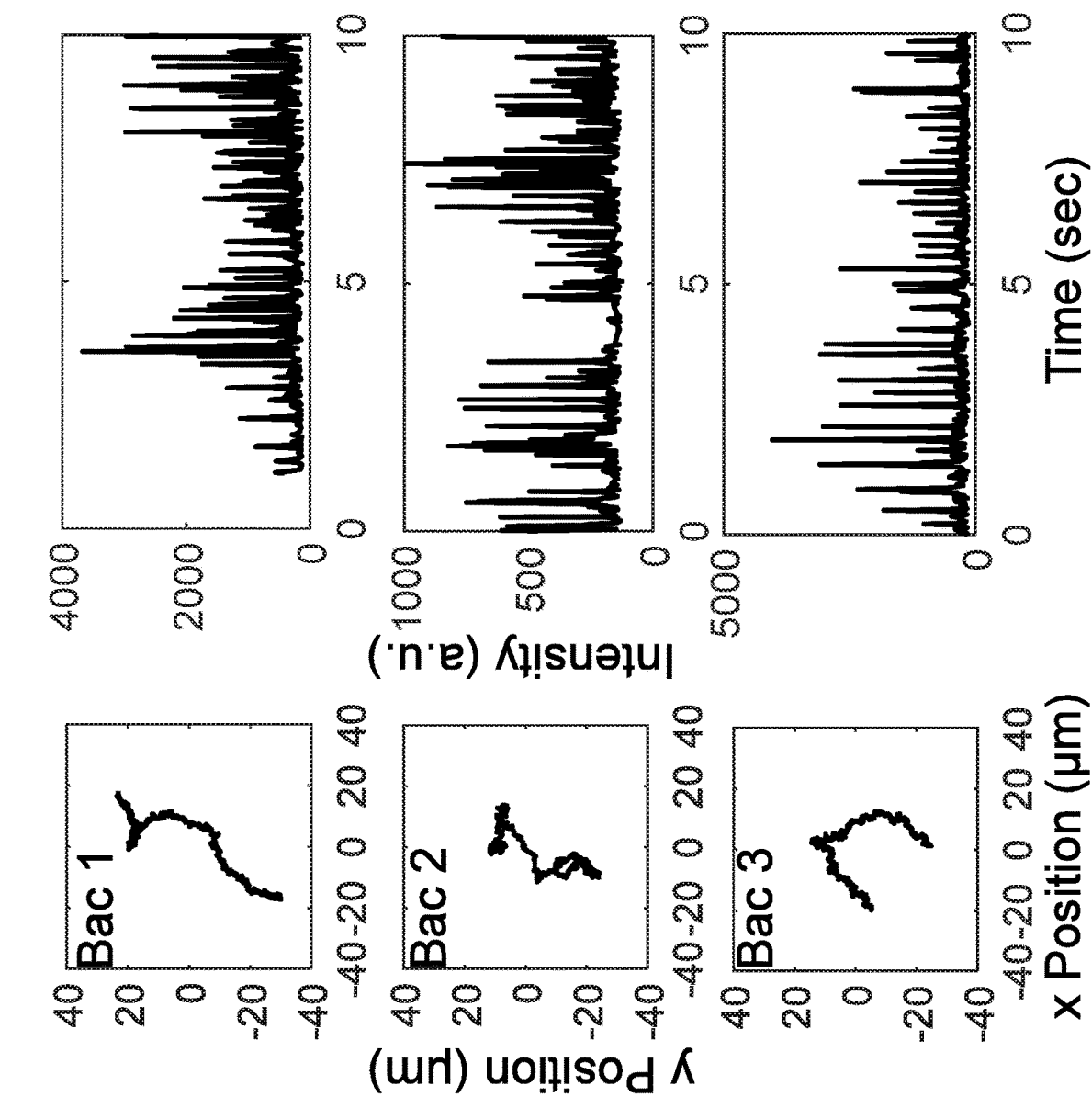
FIG. 7F shows increased magnification trajectories (left panels) and intensity profiles (right panels) of selected bacteria cells labeled in FIG. 7E.

Referring now to FIG. 7F increased magnification (left panels) and intensity profiles (right panels) of selected bacteria cells as labeled in FIG. 7E is shown.

Figure 7G:
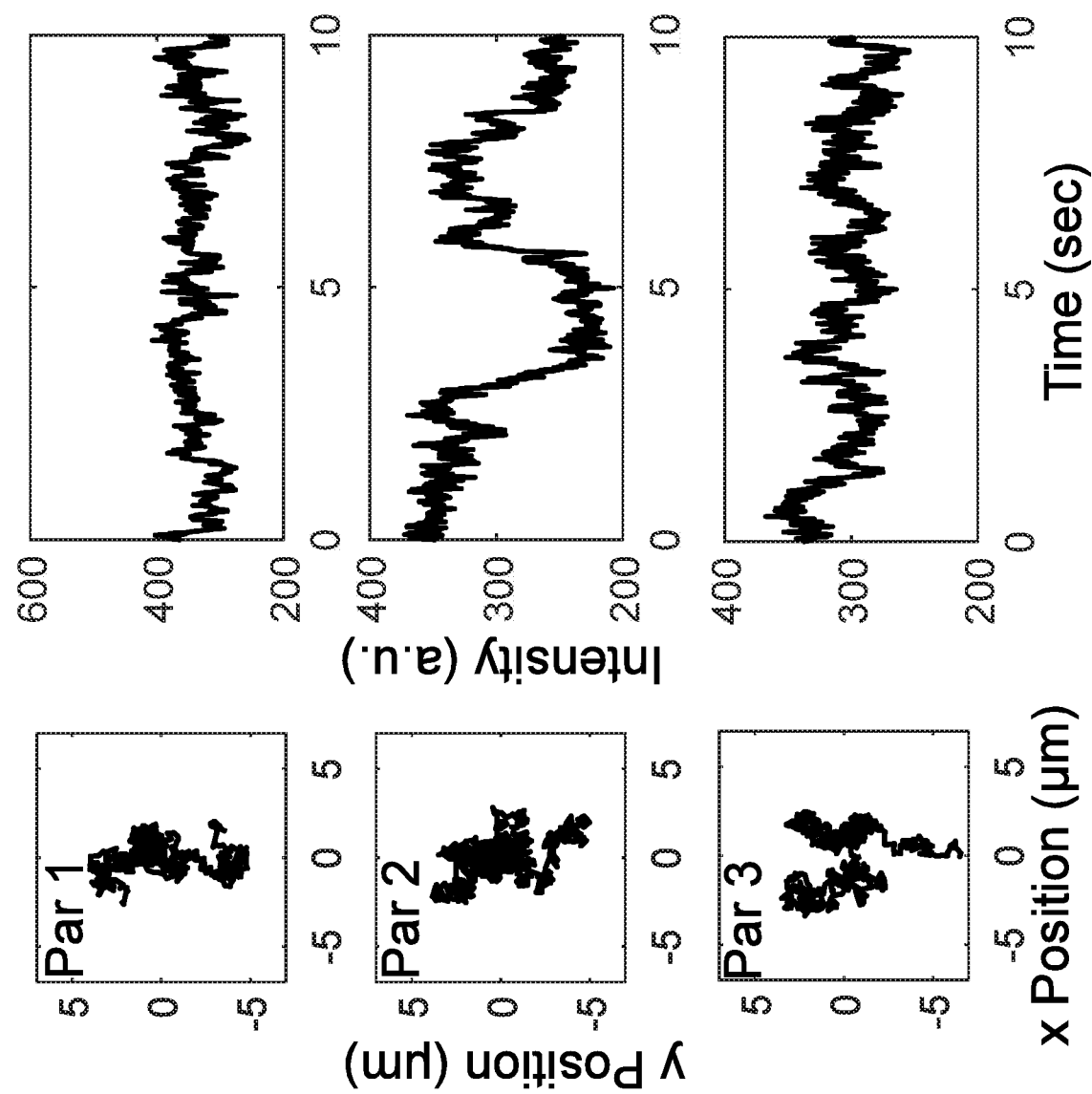
FIG. 7G shows increased magnification trajectories (left panels) and intensity profiles (right panels) of selected polystyrene particles labeled in FIG. 7E.

Referring now to FIG. 7G increased magnification trajectories (left panels) and intensity profiles (right panels) of selected polystyrene particles labeled in FIG. 7E is shown.

Identification of Bacterial Cells in Real Urine Sample

Referring now to FIG. 8A-FIG. 8D, representative frames from videos of bacteria in a subject urine sample are shown. In this example, human urine was spiked with *E. coli* bacteria. Bacteria cell images for bacteria in urine are indicated as broken circles 50. Particle images for particles in urine are indicated as broken circles 60. The scale bar in each frame is calibrated at 50 μm.

Figure 8A:
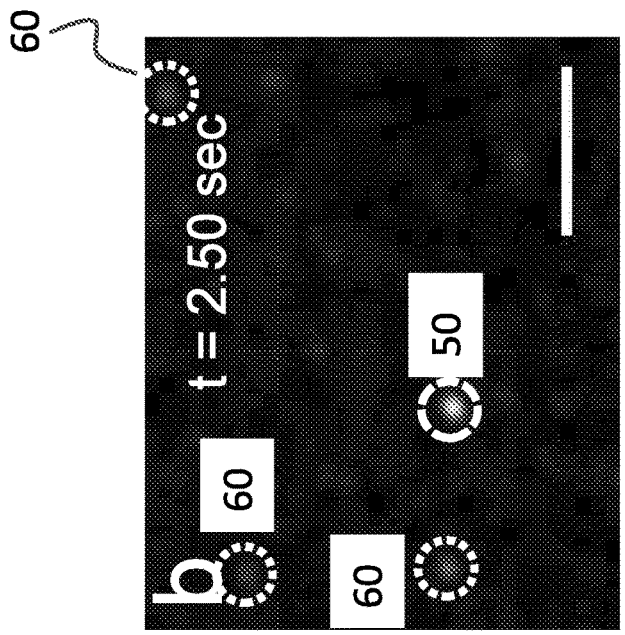
FIG. 8A-FIG. 8D show Representative frames from videos of bacteria in a human urine sample.
Figure 8B:
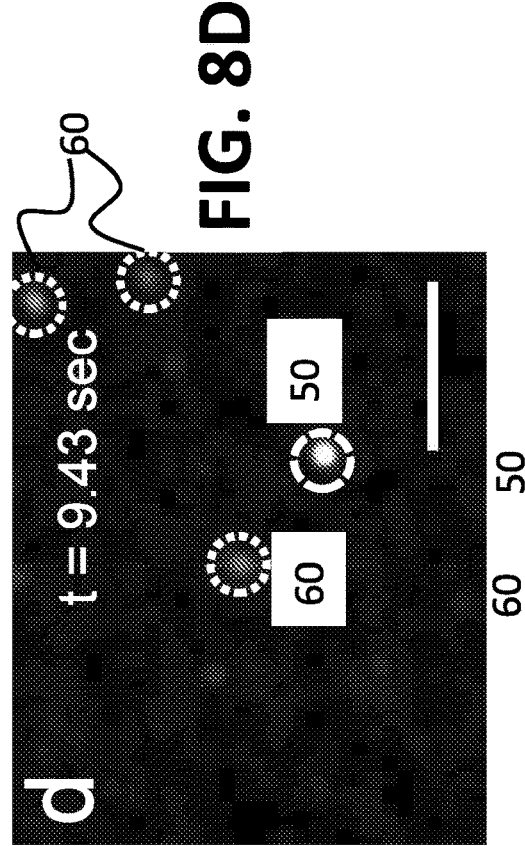
Figure 8C:
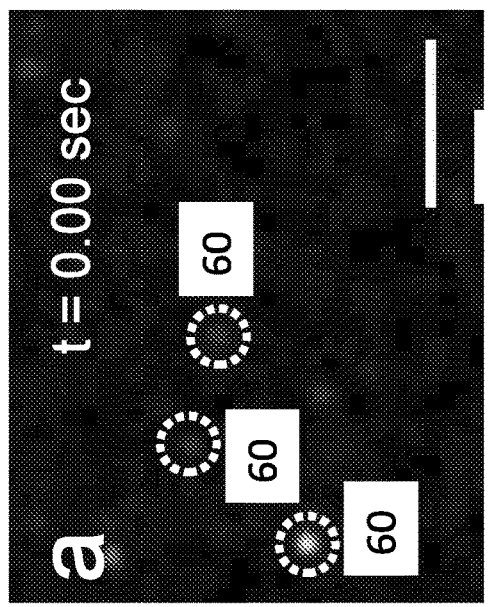
Figure 8D:
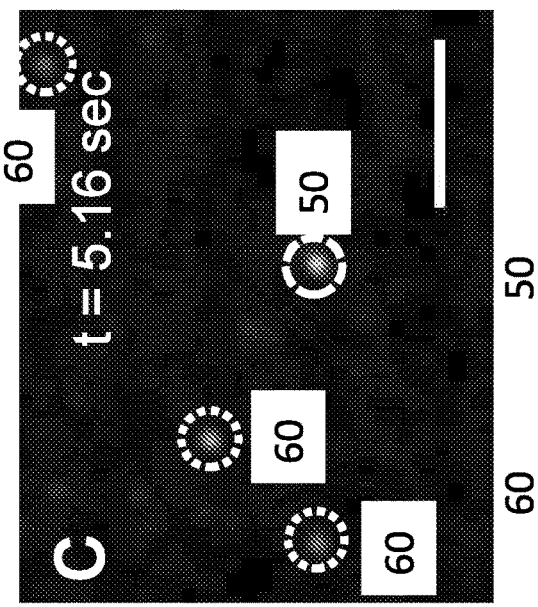
Figure 8E:
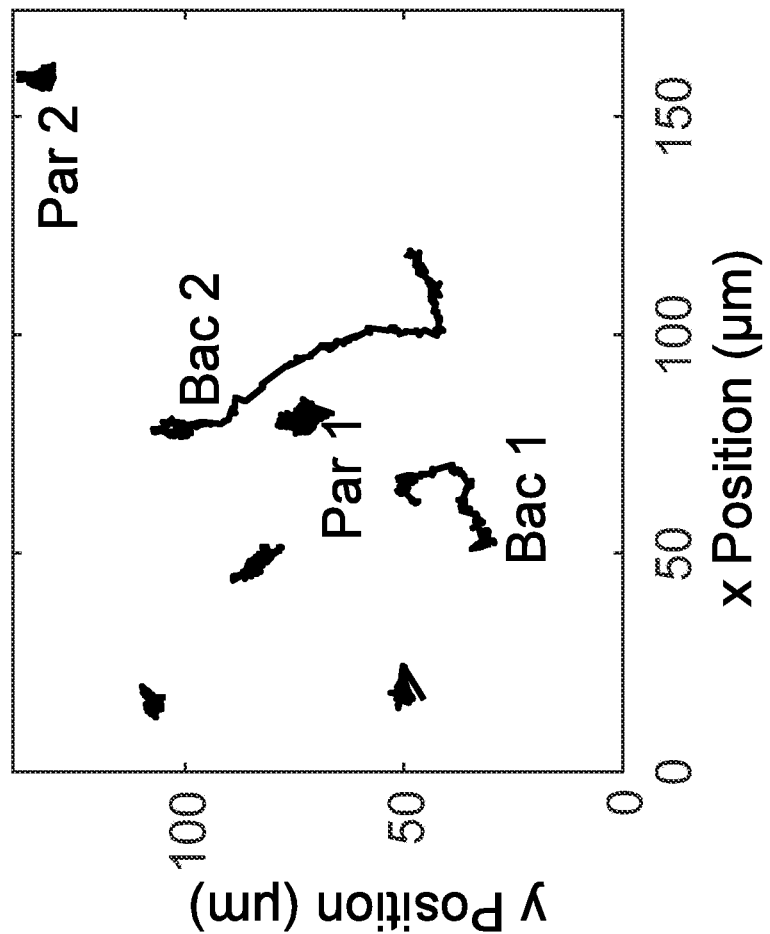
FIG. 8E shows an example Trajectories of bacteria and particles in the video.

Referring now to FIG. 8E, example trajectories of bacteria and particles in the video are shown. Particles are labeled as Par 1-2. Bacteria are labeled as Bac 1-2.

Figure 8F:
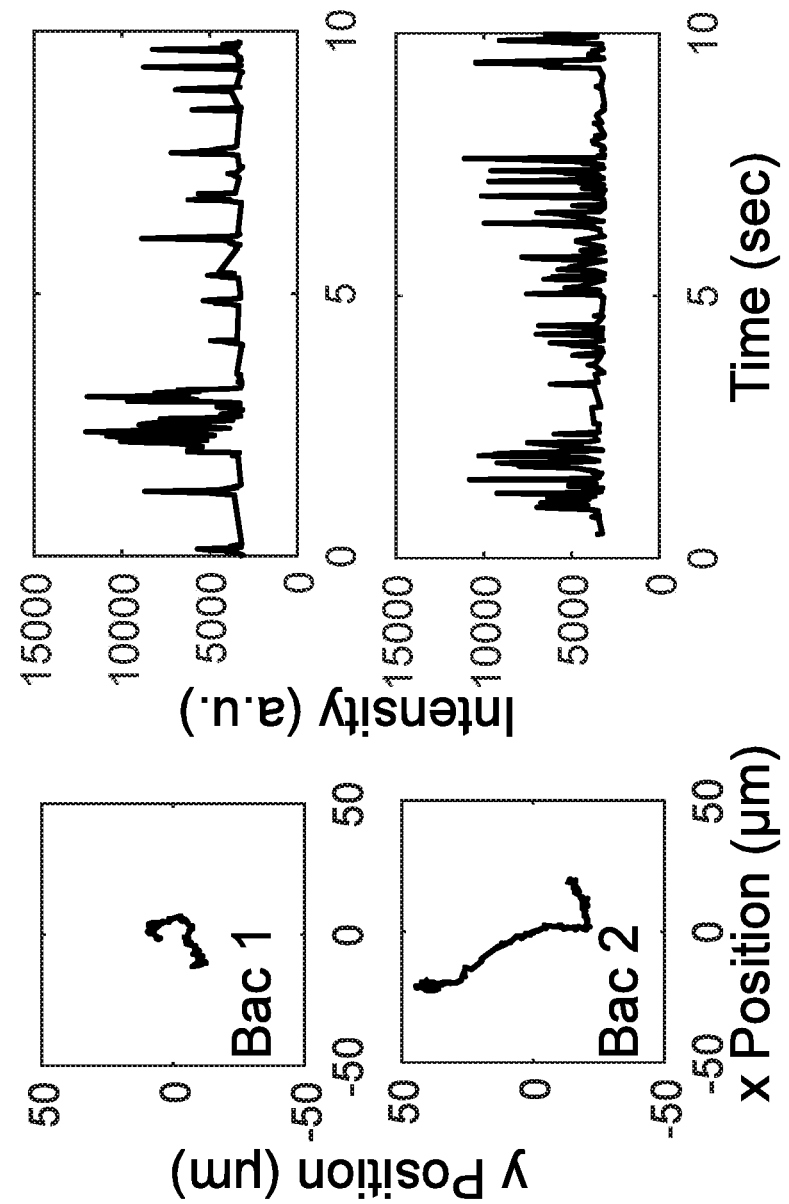
FIG. 8F shows increased magnification trajectories (left panels) and intensity profiles (right panels) of selected bacteria cells labeled in FIG. 8E.

Referring now to FIG. 8F, increased magnification trajectories (left panels) and intensity profiles (right panels) of selected bacteria cells labeled in FIG. 8E are shown.

Figure 8G:
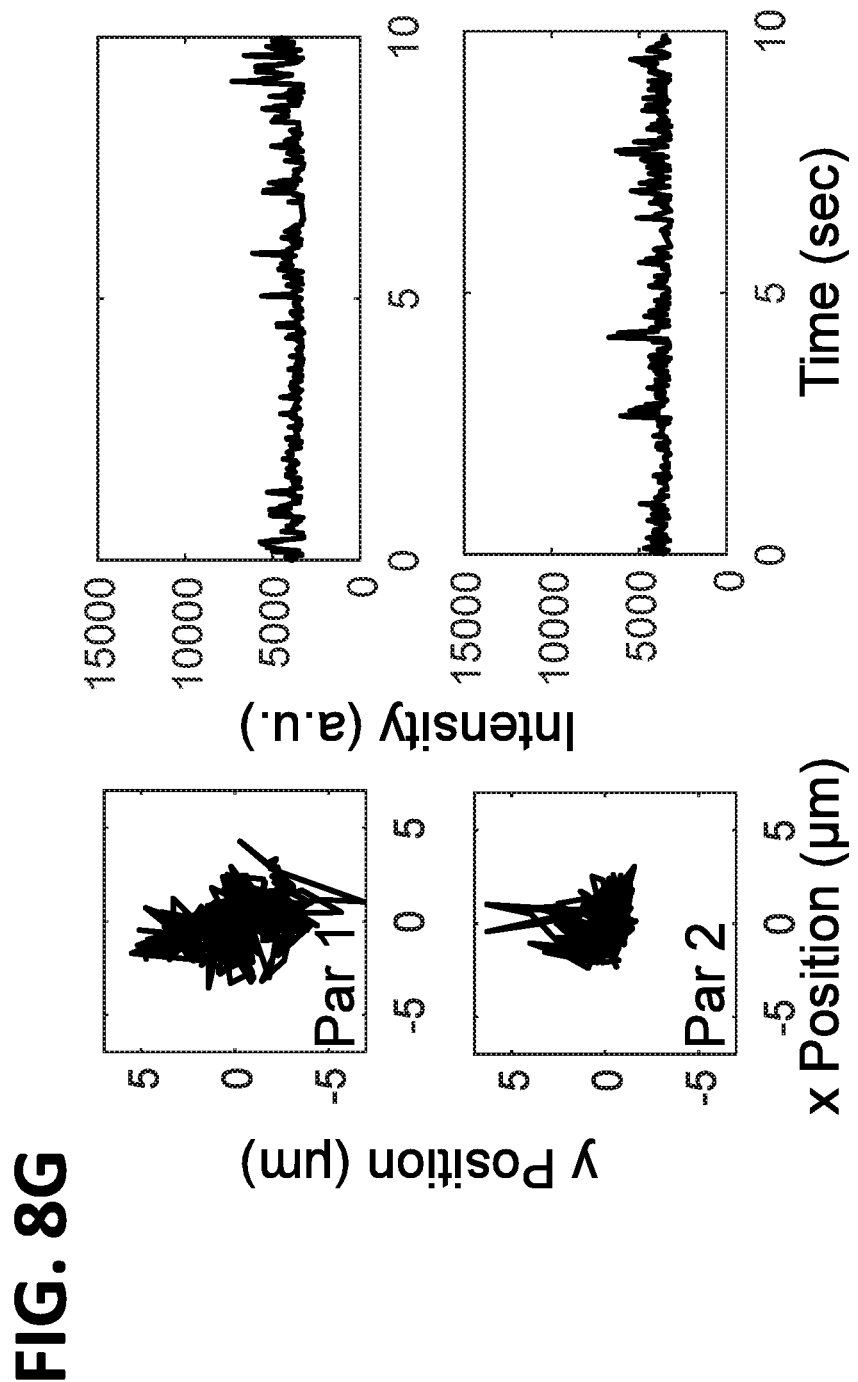
FIG. 8G increased magnification trajectories (left panels) and intensity profiles (right panels) of selected polystyrene particles labeled in FIG. 8E.

Referring now to FIG. 8G, increased magnification trajectories (left panels) and intensity profiles (right panels) of selected polystyrene particles labeled in FIG. 8E are shown.

Feature Difference from Non-Motile Bacteria

Figure 9A:
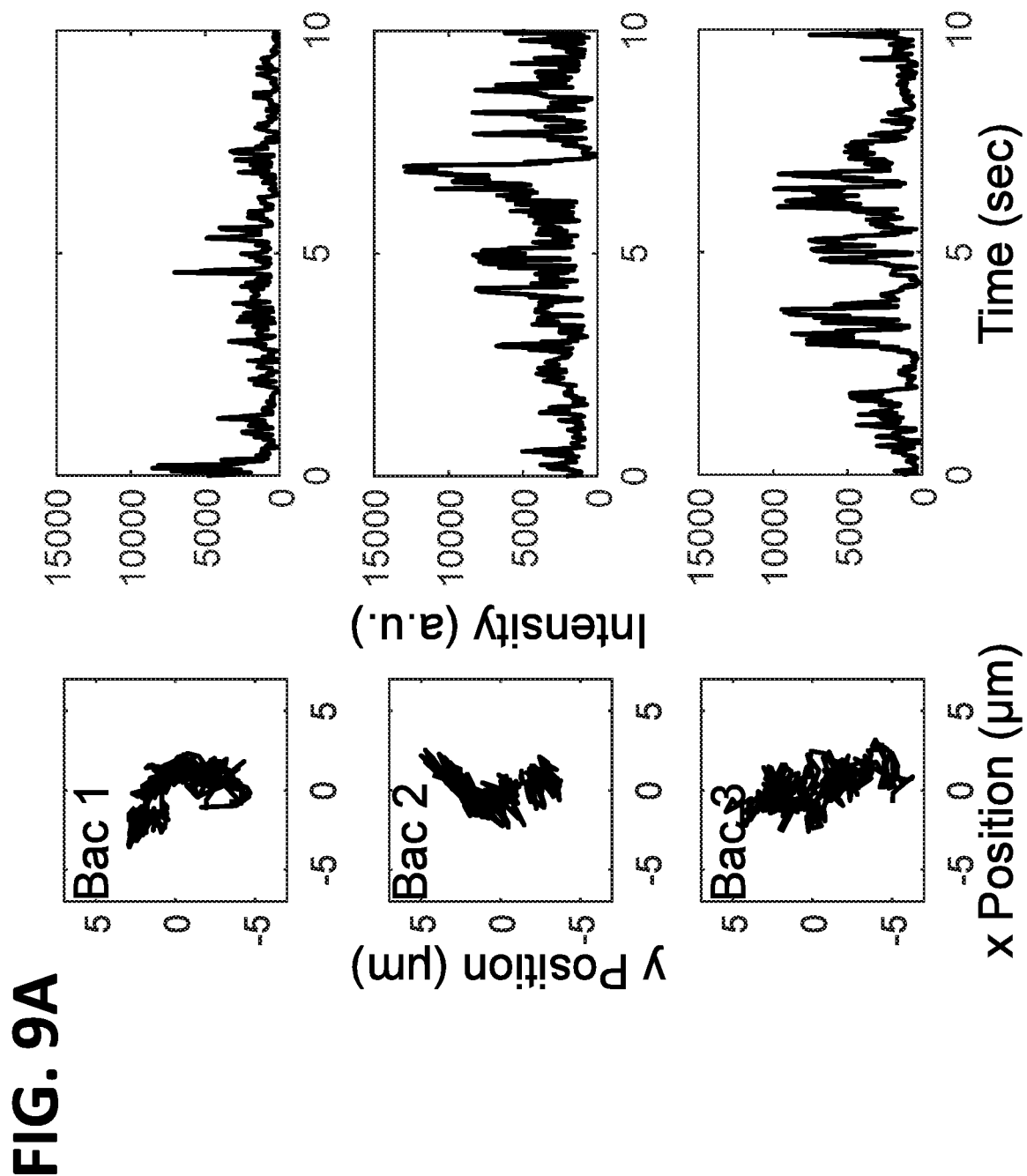
FIG. 9A shows representative position trajectory (left panels) and intensity profile (right panels) of non-motile bacteria (*Mycobacterium smegmatis*).

Referring now to FIG. 9A, representative position trajectory (left panels) and intensity profile (right panels) of non-motile bacteria (*Mycobacterium smegmatis*) are shown.

Figure 9B:
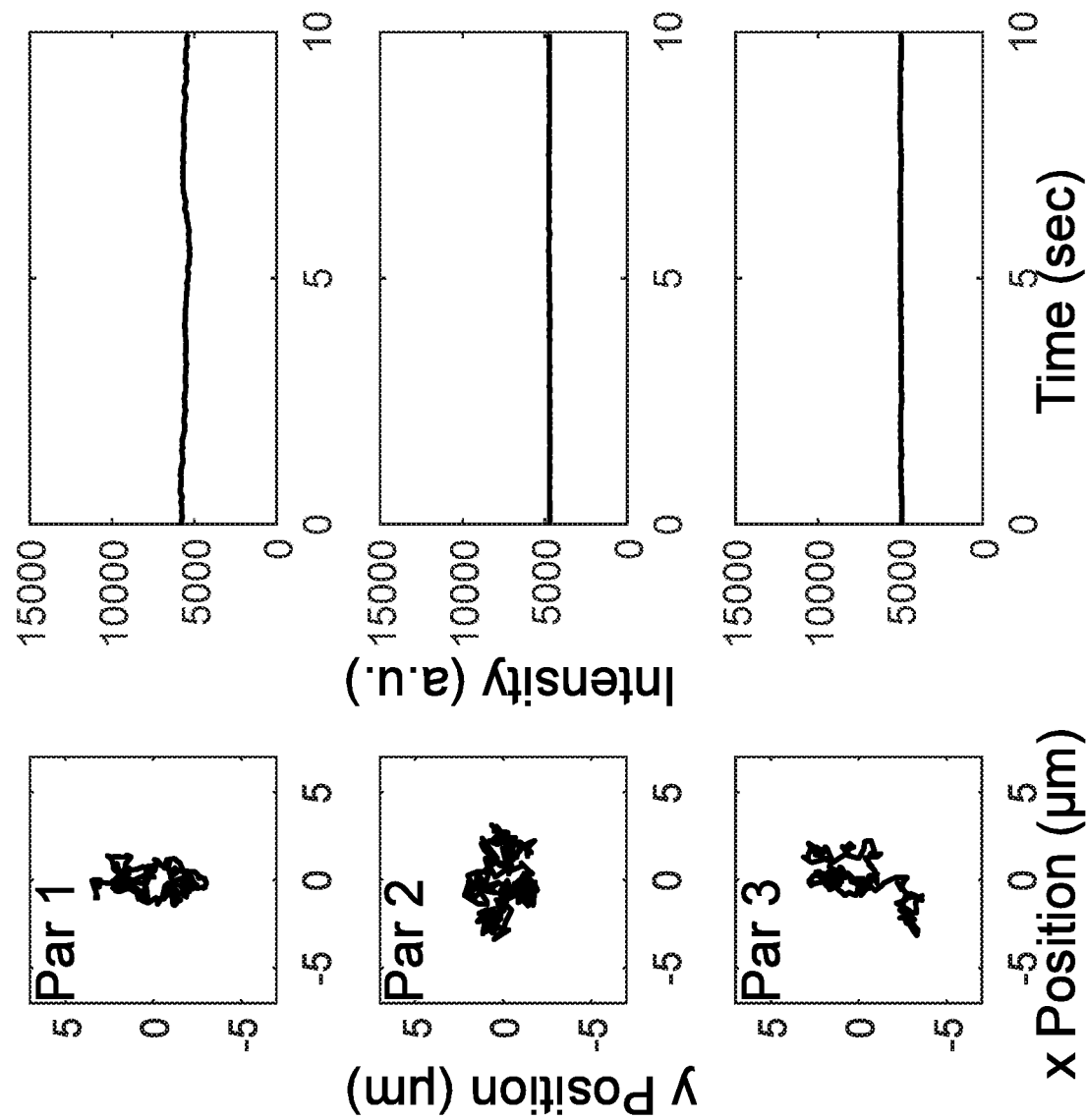
FIG. 9B shows representative position trajectory (left panels) and intensity profile (right panels) of 0.5 μm polystyrene beads.

Referring now to FIG. 9B, representative position trajectory (left panels) and intensity profile (right panels) of 0.5 μm polystyrene beads are shown.

Figure 10:
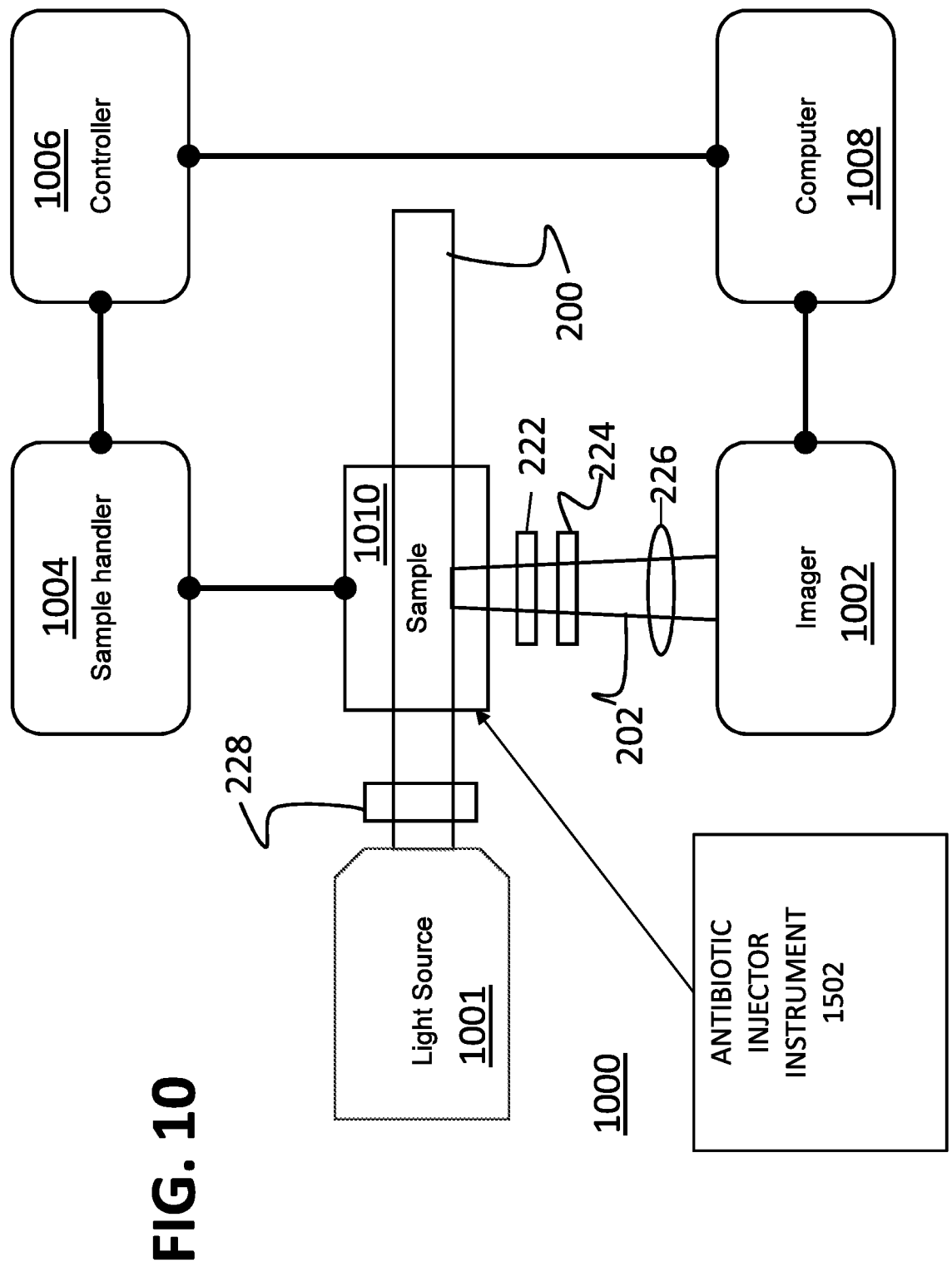
FIG. 10 illustrates an example of a setup scheme of a low amplification and large view volume light scattering microscopy.

Referring now to FIG. 10, an example of a setup scheme of a low amplification and large view volume light scattering microscopy system is illustrated. The system 1000 includes a sample 1010 illuminated with a beam 200 by a light source 1001. A scattering image 202 is collected by an imager 1002. Samples 1010 are handled by a sample handler 1004 which is coupled to a controller 1006. Images are streamed, stored and analyzed by a computer 1008, which also command the whole system.

In one example, the system comprises a light source 1001, an imager 1002 located to receive light scattered from the sample, a computer 1008 coupled to receive data transmitted from the imager 1002, a sample handler 1004 adapted to position the sample, and a controller 1006 coupled to send control signals to the sample handler and the computer. The imager processes the scattered light 202 to form images of the bacteria and transmits bacteria image information to the computer, wherein the bacteria image information includes intensity values and position data for the bacteria images.

Figure 11:
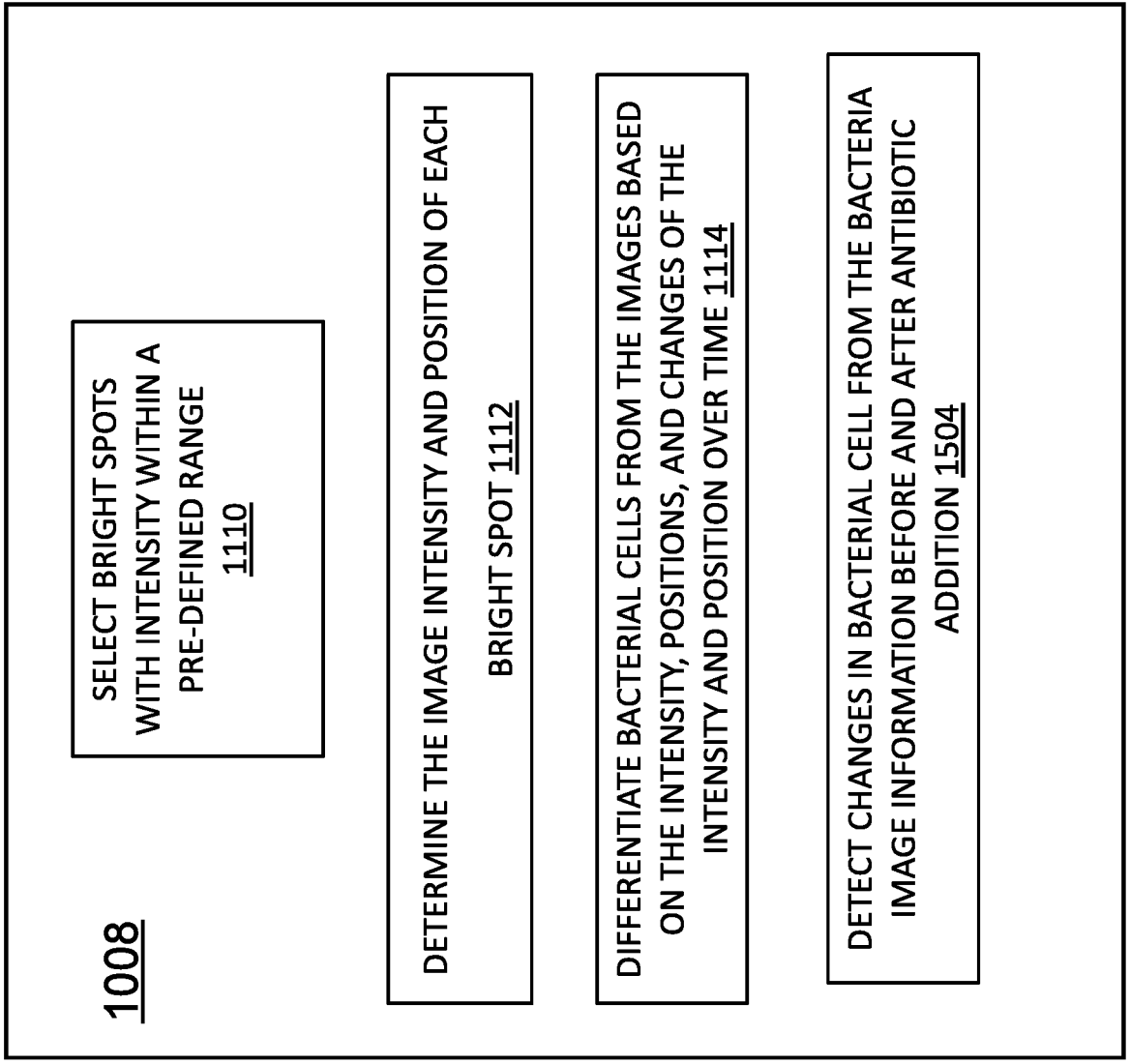
FIG. 11 shows an example of algorithms implemented in computer software or hardware for fast bacteria detection and AST testing.

Referring now jointly to FIG. 10 and FIG. 11, a more detailed view of the computer algorithms is also shown. The computer 1008 advantageously includes a first algorithm 1110 that operates to select the bright spots with intensity within a pre-defined range from the images captured by the imager. The computer further includes a second algorithm 1112 that operates to determine the image intensity and position of each bright spot. The computer further includes a third algorithm 1114 that operates to differentiate bacterial cells from the images based on the intensity, positions, and changes of the intensity and position over time. The algorithms may comprise computer software programs or may be embedded in electronic circuits in either analog or digital formats.

In another example, the imager 1002 may include two or more imagers configured to capture scattered light from two or more different angles.

In another example, the imager may further include optical components selected from the group consisting of at least one filter 222, at least one polarizer 224, at least one modulator 228 and at least one lens 226 configured to modulate the images.

Figure 12:
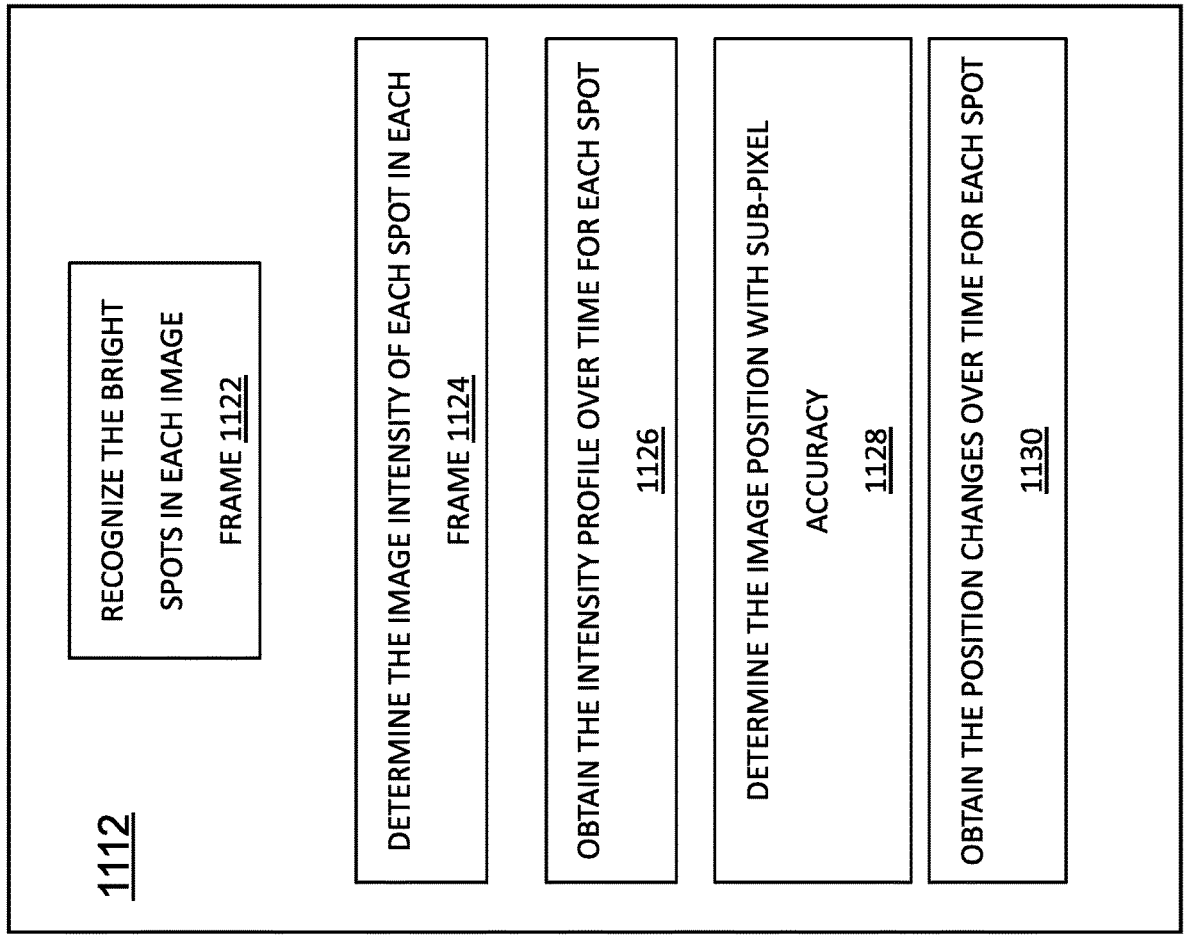

Referring now to FIG. 12, an example of additional sub-algorithms is shown. In another example, the second algorithm 1112 includes a plurality of second sub-algorithms that operate on the bacteria image information to recognize the bright spots in each image frame 1122, determine the image intensity of each spot in each frame 1124, and obtain the intensity profile over time for each spot 1126. In yet another example, the second algorithm may include a plurality of second sub-algorithms that operate on the bacteria image information to recognize the image spots in each frame; determine the image position with sub-pixel accuracy; and obtain the position changes over time for each spot.

Figure 13:
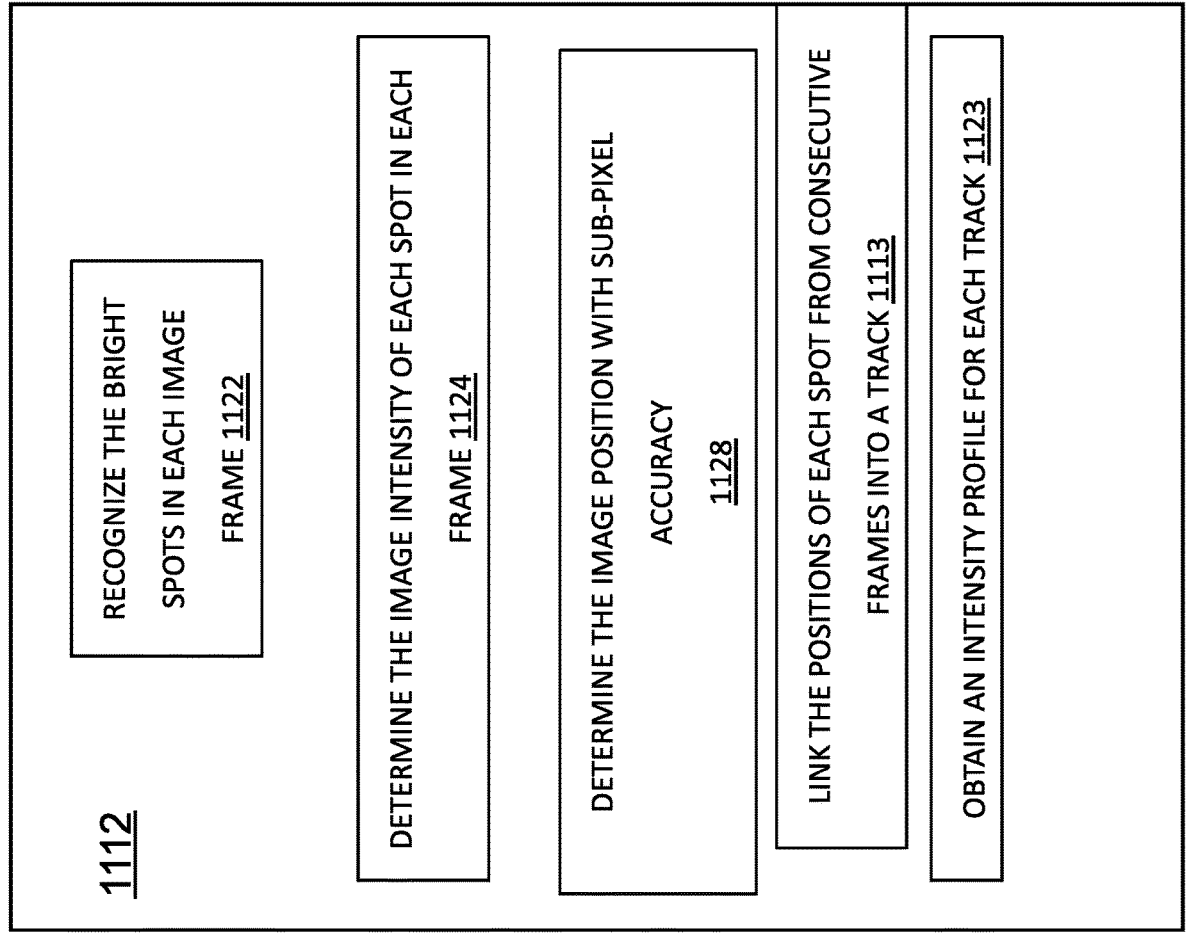

Referring now to FIG. 13, there shown are sub-algorithms employed by the system. In one example, the second algorithm may also include a plurality of third sub-algorithms that operate on the bacteria image information to recognize the bright spots in each frame 1122, determine the position of each bright spot with sub-pixel accuracy in each frame 1128, link the positions of each spot from consecutive frames into a track 1113, and obtain an intensity profile for each track 1123.

Referring now to FIG. 14, there shown are sub-algorithms employed by the system. The third algorithm 1114 may advantageously include a plurality of third sub-algorithms that operate on the bacteria image information to differentiate bacterial cells from the other micro-scale substances including extracting the average intensity of each bright spot, and comparing it with a predetermined value for a bacterial cell (with predetermined intensity range from 1000-20000 for 16 bit images for illumination using laser of ~100 mW) to determine a first feature value 1410; determining the intensity variation pattern over time, and comparing it with reference patterns for dead bacterial cells and other micro-scale substances (Intensity fluctuations at the frequency window from 5 to 40 Hz are considered as intrinsic active motion from bacteria, which is a signature for intensity pattern recognition and comparison) 1412 to determine a second feature value; analyzing the motion of the bright spot, and compare it to the Brownian motion (A linear mean square displacement over time delay is a typical signature for Brownian motion, while moving object has higher mean square displacement increase with the time delay) 1414 to determine a third feature value; detecting splitting of a bright spot into two or more spots 1416 to determine a fourth feature value; determining the total number of bright spots and track them over time 1418 to determine a fifth feature value; and combining features from the above, above features change over time, and derivatives of the above features that change over time, including mean, standard deviation, skew, kurtosis, acts and comparing them with those for dead bacterial cells and other micro-scale substances 1420.

In another example, the system can be modified to be used as a system for a fast antibiotic susceptibility test (AST) for testing an antibiotic in a sample. The system is constructed substantially identically as described above with the addition of an antibiotic injector instrument 1502 adapted to add various antibiotics at various concentrations to the sample. The antibiotic injector instrument may be any appropriate device for adding substances to a sample. For the AST system, the computer further includes a fourth algorithm 1504 that operates to detect changes in bacterial cell from the bacteria image information before and after antibiotic addition. The changes include the intensity, positions, and changes of the intensity and position over time. For either AST testing or fast detection, the bacterial cells may be selected from the group consisting of pathogenic bacteria in urine, E. coli, Salmonella, Listeria and combinations thereof. Thus, the system can be used to analyze samples related to a diagnosis of urine tract infections, food poisoning infections and the like.

In one example, a system for identification of bacteria in a free solution without immobilization includes a light source; a sample handler adapted to position the sample; an imager located to receive light scattered from the sample; a computer coupled to receive data transmitted from the imager; a controller coupled to send control signals to the sample handler and the computer; wherein the imager processes the scattered light to form images of the bacteria and transmits bacteria image information to the computer, wherein the bacteria image information includes intensity values and position data for the bacteria images; wherein the computer includes a first algorithm that operates to select the bright spots with intensity within a pre-defined range from the images captured by the imager; wherein the computer further includes a second algorithm that operates to determine the image intensity and position of each bright spot; and wherein the computer further includes a third algorithm that operates to differentiate bacterial cells from the images based on the intensity, positions, and changes of the intensity and position over time.

In one useful example, the imager is configured to image a large imaging volume such that the volume of the sample that is imaged is greater or equal to 1 µL with a low bacterial concentration of $10^5$ CFU/mL or less.

In another useful example, the computer includes an algorithm for extracting a plurality of cell features for single cells and the imager tracks the changes of the plurality of cell features over time for the single cells for further identification and antimicrobial susceptibility testing.

In yet another useful example, the computer also includes an algorithm for extracting a plurality of cell features for single cells and the imager tracks the changes of the plurality of cell features over time for the single cells for further identification and antimicrobial susceptibility testing. In yet another useful example, the computer includes an algorithm for extracting a plurality of cell features for single cells and the imager tracks the changes of the plurality of cell features over time for the single cells for further identification and antimicrobial susceptibility testing.

In another example, a system for ID/AST of a sample of bacteria in a free solution without immobilization includes a light source; a sample handler adapted to position the sample, where the sample has a clinically relevant low bacterial cell concentration; an imager located to receive light scattered from the sample, where the imager is adjusted to receive a large imaging volume (greater than $10^{-7}$ mL); a computer coupled to receive data transmitted from the imager; a controller coupled to send control signals to the sample handler and the computer; wherein the imager processes the scattered light to form images of the bacteria and transmits bacteria image information to the computer, wherein the bacteria image information includes intensity values and position data for the bacteria images, and wherein the computer further comprises an algorithm for extracting a plurality of cell features for single cells and the imager tracks the changes of the plurality of cell features over time for the single cells for further identification and antimicrobial susceptibility testing; wherein the computer includes a first algorithm that operates to select the bright spots with intensity within a pre-defined range from the images captured by the imager; wherein the computer further includes a second algorithm that operates to determine the image intensity and position of each bright spot; and wherein the computer further includes a third algorithm that operates to differentiate bacterial cells from the images based on the intensity, positions, and changes of the intensity and position over time.

In a further example, the computer also includes an algorithm for extracting a plurality of cell features for single cells and the imager tracks the changes of the plurality of cell features over time for the single cells for further identification and antimicrobial susceptibility testing.

Certain exemplary embodiments of the invention have been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

The teachings of the following references are incorporated herein in their entirety.

References Cited

1. Reller, L. B.; Weinstein, M.; Jorgensen, J. H.; Ferraro, M. J., Antimicrobial susceptibility testing: a review of general principles and contemporary practices. *Clinical infectious diseases* 2009, 49, 1749-1755.
2. Bauer, K. A.; Perez, K. K.; Forrest, G. N.; Goff, D. A., Review of rapid diagnostic tests used by antimicrobial stewardship programs. *Clinical infectious diseases* 2014, 59, S134-S145.
3. Davenport, M.; Mach, K. E.; Shortliffe, L. M. D.; Banaei, N.; Wang, T.-H.; Liao, J. C., New and developing diagnostic technologies for urinary tract infections. *Nature Reviews Urology* 2017, 14, 296.
4. Bergeron, M. G.; Ouellette, M., Preventing antibiotic resistance through rapid genotypic identification of bacteria and of their antibiotic resistance genes in the clinical microbiology laboratory. *Journal of clinical microbiology* 1998, 36, 2169-2172.
5. Palmer, A. C.; Kishony, R., Understanding, predicting and manipulating the genotypic evolution of antibiotic resistance. *Nature Reviews Genetics* 2013, 14, 243.
6. Sinn, I.; Albertson, T.; Kinnunen, P.; Breslauer, D. N.; McNaughton, B. H.; Burns, M. A.; Kopelman, R., Asynchronous magnetic bead rotation microviscometer for rapid, sensitive, and label-free studies of bacterial growth and drug sensitivity. *Analytical chemistry* 2012, 84, 5250-5256.
7. Kinnunen, P.; Sinn, I.; McNaughton, B. H.; Newton, D. W.; Burns, M. A.; Kopelman, R., Monitoring the growth and drug susceptibility of individual bacteria using asynchronous magnetic bead rotation sensors. *Biosensors and Bioelectronics* 2011, 26, 2751-2755.

8. Choi, J.; Jung, Y.-G.; Kim, J.; Kim, S.; Jung, Y.; Na, H.; Kwon, S., Rapid antibiotic susceptibility testing by tracking single cell growth in a microfluidic agarose channel system. *Lab on a Chip* 2013, 13, 280-287.

9. Choi, J.; Yoo, J.; Lee, M.; Kim, E.-G.; Lee, J. S.; Lee, S.; Joo, S.; Song, S. H.; Kim, E.-C.; Lee, J. C., A rapid antimicrobial susceptibility test based on single-cell morphological analysis. *Science translational medicine* 2014, 6, 267ra174-267ra174.

10. Douglas, I. S.; Price, C. S.; Overdier, K. H.; Wolken, R. F.; Metzger, S. W.; Hance, K. R.; Howson, D. C., Rapid automated microscopy for microbiological surveillance of ventilator-associated pneumonia. *American journal of respiratory and critical care medicine* 2015, 191, 566-573.

11. Chantell, C., Multiplexed automated digital microscopy for rapid identification and antimicrobial susceptibility testing of bacteria and yeast directly from clinical samples. *Clinical Microbiology Newsletter* 2015, 37, 161-167.

12. Lu, Y.; Gao, J.; Zhang, D. D.; Gau, V.; Liao, J. C.; Wong, P. K., Single cell antimicrobial susceptibility testing by confined microchannels and electrokinetic loading. *Analytical chemistry* 2013, 85, 3971-3976.

13. Chen, C. H.; Lu, Y.; Sin, M. L.; Mach, K. E.; Zhang, D. D.; Gau, V.; Liao, J. C.; Wong, P. K., Antimicrobial susceptibility testing using high surface-to-volume ratio microchannels. *Analytical chemistry* 2010, 82, 1012-1019.

14. Besant, J. D.; Sargent, E. H.; Kelley, S. O., Rapid electrochemical phenotypic profiling of antibiotic-resistant bacteria. *Lab on a Chip* 2015, 15, 2799-2807.

15. Ertl, P.; Robello, E.; Battaglini, F.; Mikkelsen, S. R., Rapid Antibiotic Susceptibility Testing via Electrochemical Measurement of Ferricyanide Reduction by *Escherichia coli* and *Clostridium sporogenes*. *Analytical chemistry* 2000, 72, 4957-4964.

16. Chotinantakul, K.; Suginta, W.; Schulte, A., Advanced amperometric respiration assay for antimicrobial susceptibility testing. *Analytical chemistry* 2014, 86, 10315-10322.

17. Longo, G.; Alonso-Sarduy, L.; Rio, L. M.; Bizzini, A.; Trampuz, A.; Notz, J.; Dietler, G.; Kasas, S., Rapid detection of bacterial resistance to antibiotics using AFM cantilevers as nanomechanical sensors. *Nature nanotechnology* 2013, 8, 522.

18. Aghayee, S.; Benadiba, C.; Notz, J.; Kasas, S.; Dietler, G.; Longo, G., Combination of fluorescence microscopy and nanomotion detection to characterize bacteria. *Journal of Molecular Recognition* 2013, 26, 590-595.

19. Lissandrello, C.; Inci, F.; Francom, M.; Paul, M.; Demirci, U.; Ekinci, K., Nanomechanical motion of *Escherichia coli* adhered to a surface. *Applied physics letters* 2014, 105, 113701.

20. Syal, K.; Iriya, R.; Yang, Y.; Yu, H.; Wang, S.; Haydel, S. E.; Chen, H.-Y.; Tao, N., Antimicrobial susceptibility test with plasmonic imaging and tracking of single bacterial motions on nanometer scale. *ACS nano* 2015, 10, 845-852.

21. Syal, K.; Shen, S.; Yang, Y.; Wang, S.; Haydel, S. E.; Tao, N., Rapid antibiotic susceptibility testing of uropathogenic *E. coli* by tracking submicron scale motion of single bacterial cells. *ACS sensors* 2017, 2, 1231-1239.

22. Yu, H.; Jing, W.; Iriya, R.; Yang, Y.; Syal, K.; Mo, M.; Grys, T. E.; Haydel, S. E.; Wang, S.; Tao, N., Phenotypic antimicrobial susceptibility testing with deep learning video microscopy. *Analytical chemistry* 2018, 90, 6314-6322.

23. Baltekin, Ö.; Boucharin, A.; Tano, E.; Andersson, D. I.; Elf, J., Antibiotic susceptibility testing in less than 30 min using direct single-cell imaging. *Proceedings of the National Academy of Sciences* 2017, 114, 9170-9175.

24. Schoepp, N. G.; Schlappi, T. S.; Curtis, M. S.; Butkovich, S. S.; Miller, S.; Humphries, R. M.; Ismagilov, R. F., Rapid pathogen-specific phenotypic antibiotic susceptibility testing using digital LAMP quantification in clinical samples. *Science translational medicine* 2017, 9, eaal3693.

25. Metzger, S. W.; Howson, D. C.; Goldberg, D. A.; Buttry, D. A., Rapid microbial detection and antimicrobial susceptibility testing. Google Patents: 2008.

What is claimed is:

1. A system for identification of bacteria in a free solution without immobilization, comprising:
   a light source to illuminate a volume in the range of $10^{-5} \sim 10^{-2}$ mL;
   a sample handler adapted to position the sample;
   an imager located to receive light scattered from the sample;
   a computer coupled to receive data transmitted from the imager;
   a controller coupled to send control signals to the sample handler and the computer;
   wherein the imager processes the scattered light to form images of the bacteria and transmits bacteria image information to the computer, wherein the bacteria image information includes intensity values and position data for the bacteria images;
   wherein the computer includes a first algorithm that operates to select the bright spots with intensity within a pre-defined range from the images captured by the imager;
   wherein the computer further includes a second algorithm that operates to determine the image intensity and position of each bright spot; and
   wherein the computer further includes a third algorithm that operates to differentiate bacterial cells from the images based on the intensity, positions, and changes of the intensity and position over time.

2. The system of claim 1 wherein the imager comprises two or more imagers configured to capture scattered light from two or more different angles.

3. The system of claim 1 further wherein the imager further comprises optical components selected from the group consisting of at least one polarizer, at least one filter, at least one modulator and at least one lens configured to modulate the images.

4. The system of claim 1 wherein the second algorithm includes a plurality of second sub-algorithms that operate on the bacteria image information to recognize bright spots representing bacteria in each image frame; to determine the image intensity of each spot in each frame; and to obtain the intensity profile over time for each spot.

5. The system of claim 1 wherein the second algorithm includes a plurality of second sub-algorithms that operate on the bacteria image information to recognize the image spots in each frame; determine the image position with sub-pixel accuracy; and obtain the position changes over time for each spot.

6. The system of claim 1 wherein the second algorithm includes a plurality of third sub-algorithms that operate on the bacteria image information to recognize the bright spots in each frame; determine the position of each bright spot with sub-pixel accuracy in each frame; link the positions of each spot from consecutive frames into a track; and obtain an intensity profile for each track.

7. The system of claim 1 wherein the third algorithm includes a plurality of third sub-algorithms that operate on the bacteria image information to differentiate bacterial cells from the other micro-scale substances by extracting a plurality of features including extracting the average intensity of each bright spot, and comparing it with a predetermined value for a bacterial cell to determine a first feature value;

determining the intensity variation pattern over time, and comparing it with reference patterns for dead bacterial cells and other micro-scale substances to determine a second feature value; analyzing the motion of the bright spot, and compare it to Brownian motion to determine a third feature value; detecting splitting of a bright spot into two or more spots to determine a fourth feature value; determining the total number of bright spots and tracking them over time to determine a fifth feature value; and combining the above listed feature values and comparing them with features for dead bacterial cells and other micro-scale substances.

8. A system for a fast antibiotic susceptibility test (AST) for testing an antibiotic in a sample comprising:

a light source to illuminate a volume of sample in the range of $10^{-5} \sim 10^{-2}$ an imager located to receive light scattered from the illuminated volume of the sample at one or more angles;

a computer coupled to receive data transmitted from the imager;

a sample handler adapted to position the sample, wherein the sample consists of bacterial cells in free solution;

a controller coupled to send control signals to the sample handler and the computer;

wherein the imager processes the scattered light to form images of the bacteria and transmits bacteria image information to the computer, wherein the bacteria image information includes intensity values and position data for the bacteria images;

wherein the computer includes a first algorithm that operates to select the bright spots with intensity within a pre-defined range from the images captured by the imager; wherein the computer further includes a second algorithm that operates to determine the image intensity and position of each bright spot; and wherein the computer further includes a third algorithm that operates to differentiate bacterial cells from the images based on the intensity, positions, and changes of the intensity and position over time.

9. The system of claim 8 wherein the changes include the intensity, positions, and changes of the intensity and position over time.

10. The system of claim 8 wherein the bacterial cells are selected from the group consisting of pathogenic bacteria in urine, *E. coli, Salmonella*, and *Listeria*.

11. The system of claim 8 further adapted to add various antibiotics at various concentrations to the sample; and wherein the computer further includes a fourth algorithm that operates to detect changes in bacterial cell from the bacteria image information before and after antibiotic addition.

12. A method for identification of bacterial cells in a sample, comprising:

obtaining a sample including biological objects, where the biological objects include bacterial cells in free solution;

illuminating a substantially large volume of the sample to produce scattered light from the sample;

receiving the scattered light;

operating an imager to transform the scattered light into imaging data;

operating a computer coupled to receive the imaging data;

wherein the imaging data includes intensity values and position data for the bacteria images including bright spots representing bacteria;

selecting the bright spots with intensity within a pre-defined range from the images captured by the imager; and determining the image intensity and position of each bright spot; and differentiating bacterial cell images from other images based on the intensity, positions, and changes of the intensity and position over time.

13. The method of claim 12 wherein the imaging data includes comprise two or more scattered light captured from two or more different angles.

14. The method of claim 12 wherein the imager further comprises optical components selected from the group consisting of at least one polarizer, at least one filter, at least one modulator and at least one lens configured to modulate the images.

15. The method of claim 12 further comprising recognizing the bright spots in each image frame; determining the image intensity of each spot in each frame; and obtaining the intensity profile over time for each spot.

16. The method of claim 12 further comprising recognizing the image spots in each frame; determining the image position with sub-pixel accuracy; and obtaining the position changes over time for each spot.

17. The method of claim 12 further comprising recognizing the bright spots in each frame; determining the position of each bright spot with sub-pixel accuracy in each frame; linking the positions of each spot from consecutive frames into a track; and generating an intensity profile for each track.

18. The method of claim 12 further comprising differentiating bacterial cells from the other micro-scale substances including extracting the average intensity of each bright spot, and comparing it with a predetermined value for a bacterial cell to determine a first feature value;

determining the intensity variation pattern over time, and comparing it with reference patterns for dead bacterial cells and other micro-scale substances to determine a second feature value;

analyzing the motion of the bright spot, and comparing it to Brownian motion to determine a third feature value;

detecting splitting of a bright spot into two or more spots to determine a fourth feature value;

determining the total number of bright spots and tracking them over time to determine a fifth feature value; and combining the first through fifth feature values, monitoring above features and derivatives of the above features including mean, standard deviation, skew, kurtosis that change over time, and comparing them with those for dead bacterial cells and other micro-scale substances.

19. A method for a fast antibiotic susceptibility test (AST) for testing an antibiotic in a sample comprising:

obtaining a sample including biological objects;

illuminating the sample to produce scattered light from the sample;

receiving the scattered light;

operating an imager to transform the scattered light into imaging data;

operating a computer coupled to receive the imaging data;

wherein the imaging data includes intensity values and position data for the bacteria images including bright spots representing bacteria;

selecting the bright spots with intensity within a predefined range from the images captured by the imager;

determining the image intensity and position of each bright spot; and differentiating bacterial cell images from other images based on the intensity, positions, and changes of the intensity and position over time;

operating an instrument to add various antibiotics at various concentrations to the sample; and detecting changes in bacterial cell from the bacteria image information before and after antibiotic addition.

20. The method of claim 19 wherein the changes include the intensity, positions, and changes of the intensity and position over time.

21. The method of claim 19 wherein the bacterial cells are selected from the group consisting of pathogenic bacteria in urine, *E. coli, Salmonella*, and *Listeria*.

\* \* \* \* \*